US008715257B2

(12) United States Patent
Dorschner

(10) Patent No.: US 8,715,257 B2
(45) Date of Patent: May 6, 2014

(54) RATIO OF ABSORBENT AREA TO OUTER PERIPHERAL AREA FOR DISPOSABLE ABSORBENT ARTICLES

(75) Inventor: Linda M. Dorschner, Kaukauna, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2014 days.

(21) Appl. No.: 10/034,846

(22) Filed: Dec. 28, 2001

(65) Prior Publication Data

US 2003/0125695 A1  Jul. 3, 2003

(51) Int. Cl.
*A61F 13/15* (2006.01)

(52) U.S. Cl.
USPC ............ 604/385.01; 604/385.19; 604/385.22; 604/385.24; 604/385.3; 604/365; 604/370; 604/372; 604/393; 604/396

(58) Field of Classification Search
USPC ............ 604/385.01, 385.19, 385.22, 385.24, 604/385.3, 365, 370, 372, 393–396
See application file for complete search history.

(56) References Cited

U.S. PATENT DOCUMENTS

| | | | |
|---|---|---|---|
| 3,502,538 A * | 3/1970 | Petersen | 428/359 |
| 3,855,045 A * | 12/1974 | Brock | 428/198 |
| 3,914,497 A * | 10/1975 | Kanehira et al. | 442/170 |
| 4,663,220 A | 5/1987 | Wisneski et al. | |
| 4,695,278 A * | 9/1987 | Lawson | 604/385.27 |
| 4,704,116 A | 11/1987 | Enloe | |
| 4,756,709 A * | 7/1988 | Stevens | 604/385.22 |
| 4,761,322 A * | 8/1988 | Raley | 428/198 |
| 4,777,073 A | 10/1988 | Sheth | |
| 4,798,603 A | 1/1989 | Meyer et al. | |
| 4,834,735 A * | 5/1989 | Alemany et al. | 604/368 |
| 4,895,568 A | 1/1990 | Enloe | |
| 4,965,122 A | 10/1990 | Morman | |
| 5,114,781 A | 5/1992 | Morman | |
| 5,116,662 A | 5/1992 | Morman | |
| 5,151,092 A * | 9/1992 | Buell et al. | 604/385.3 |
| 5,176,668 A | 1/1993 | Bernardin | |
| 5,176,672 A | 1/1993 | Bruemmer et al. | |
| 5,192,606 A | 3/1993 | Proxmire et al. | |
| 5,226,992 A | 7/1993 | Morman | |
| 5,246,433 A * | 9/1993 | Hasse et al. | 604/396 |

(Continued)

FOREIGN PATENT DOCUMENTS

| | | |
|---|---|---|
| EP | 0 217 032 | 4/1987 |
| EP | 0 382 022 | 8/1990 |

(Continued)

OTHER PUBLICATIONS

"Nonwoven", Materials handbook, 13th ed. p. 565-566.*

(Continued)

*Primary Examiner* — Tatyana Zalukaeva
*Assistant Examiner* — Ginger T Chapman
(74) *Attorney, Agent, or Firm* — Armstrong Teasdale LLP

(57) ABSTRACT

A disposable absorbent article has an absorbent core having a surface area and a stretchable multilayer chassis having a surface area. The multilayer chassis is stretchable in at least the cross-machine direction. The stretchable multilayer chassis has at least a stretchable bodyside liner and stretchable outer cover such that the absorbent core is affixed to at least one layer of the stretchable multilayer chassis. The percentage ratio of the surface area of the absorbent core to the surface area of the stretchable multilayer chassis is less than about 50%.

20 Claims, 8 Drawing Sheets

(56) References Cited

U.S. PATENT DOCUMENTS

| | | | |
|---|---|---|---|
| 5,330,457 A * | 7/1994 | Cohen | 604/378 |
| 5,358,500 A * | 10/1994 | Lavon et al. | 604/385.29 |
| 5,383,871 A * | 1/1995 | Carlin et al. | 604/385.29 |
| 5,425,726 A | 6/1995 | Shimizu et al. | |
| 5,470,640 A * | 11/1995 | Modrak | 428/171 |
| 5,486,166 A | 1/1996 | Bishop et al. | |
| 5,490,846 A | 2/1996 | Ellis et al. | |
| 5,496,298 A | 3/1996 | Kuepper et al. | |
| 5,509,915 A | 4/1996 | Hanson et al. | |
| 5,518,801 A * | 5/1996 | Chappell et al. | 428/152 |
| 5,540,796 A | 7/1996 | Fries | |
| 5,554,145 A * | 9/1996 | Roe et al. | 604/385.3 |
| 5,582,903 A | 12/1996 | Levy et al. | |
| 5,595,618 A | 1/1997 | Fries et al. | |
| 5,626,571 A * | 5/1997 | Young et al. | 604/370 |
| 5,634,916 A * | 6/1997 | Lavon et al. | 604/385.22 |
| 5,643,242 A * | 7/1997 | Lavon et al. | 604/385.21 |
| 5,652,194 A | 7/1997 | Dyer et al. | |
| 5,789,065 A | 8/1998 | Haffner et al. | |
| 5,797,895 A * | 8/1998 | Widlund et al. | 604/385.24 |
| 5,836,930 A | 11/1998 | Lantz et al. | |
| 5,883,028 A | 3/1999 | Morman et al. | |
| 5,885,264 A | 3/1999 | Matsushita | |
| 5,891,124 A | 4/1999 | Nomura et al. | |
| 5,904,673 A * | 5/1999 | Roe et al. | 604/385.3 |
| 5,914,184 A | 6/1999 | Morman | |
| 5,932,497 A | 8/1999 | Morman et al. | |
| 6,001,460 A | 12/1999 | Morman et al. | |
| 6,042,575 A | 3/2000 | Osborn, III et al. | |
| 6,060,115 A | 5/2000 | Borowski et al. | |
| 6,129,720 A | 10/2000 | Blenke et al. | |
| 6,132,411 A * | 10/2000 | Huber et al. | 604/385.29 |
| 6,169,225 B1 | 1/2001 | Otsubo | |
| 6,193,701 B1 | 2/2001 | Van Gompel et al. | |
| 6,210,387 B1 * | 4/2001 | Rudberg et al. | 604/385.27 |
| 6,245,401 B1 | 6/2001 | Ying et al. | |
| 6,321,557 B1 | 11/2001 | Scrivener et al. | |
| 6,610,383 B1 * | 8/2003 | Morman et al. | 428/152 |

FOREIGN PATENT DOCUMENTS

| | | | |
|---|---|---|---|
| EP | 0 581 044 | 2/1994 | |
| EP | 650714 A1 * | 5/1995 | A61F 13/15 |
| EP | 0 661 031 | 7/1995 | |
| GB | 2282054 A * | 3/1995 | A41B 9/04 |
| WO | 96/18367 | 6/1996 | |
| WO | WO 00/38913 A1 * | 7/2000 | |
| WO | 01/82851 | 11/2001 | |

OTHER PUBLICATIONS

Definition of "essentially", Merriam-Webster OnLine.*
International Search Report dated Feb. 17, 2003 in PCT/US 02/37329.

* cited by examiner

FIG. 7

| TABLE 1 | RATIO OF THE ABSORBENT AREA TO EXTENSIBLE CHASSIS AREA @ 0% | RATIO OF THE ABSORBENT AREA TO EXTENSIBLE CHASSIS AREA @ 16% | RATIO OF THE ABSORBENT AREA TO EXTENSIBLE CHASSIS AREA @ 29% |
|---|---|---|---|
| MEAN % STRAIN @ 500g | 21.8 | 17 | 13.1 |
| MEAN % STRAIN @ 1000g | 40.4 | 33.3 | 27.5 |
| MEAN % STRAIN @ 1400g | 47.7 | 41.8 | 37.8 |
| STDV % STRAIN @ 500g | 1.0 | 1.0 | 0.6 |
| STDV % STRAIN @ 1000g | 1.9 | 1.3 | 1.0 |
| STDV % STRAIN @ 1400g | 2.7 | 1.0 | 1.3 |

RATIO OF ABSORBENT AREA TO OUTER PERIPHERAL AREA FOR DISPOSABLE ABSORBENT ARTICLES

BACKGROUND OF THE INVENTION

Various techniques and materials have been employed in the construction of disposable absorbent articles such as diapers, in order to provide the user with desired levels of appearance, fit and leakage containment.

In particular, conventional diapers employ various constructions in order to increase the stretchability of the diaper to better fit the wearer and to be resilient to the different stresses imposed by the size and movements of the wearer without compromising the absorption capability of the absorbent core.

For example, conventional diapers have typically employed stretchable components such as waist and leg elastics, elasticized panels and the like. Further, diaper designs having stretchable components may employ folded pleats in the absorbent and in the tissue to provide improved fit and containment.

However, diapers that utilize pleats require precise folding equipment adding to the complexity and cost of the diaper construction. In addition, the extension of the diaper facings may be inhibited by the friction of the absorbent core and the outer cover sliding over each other, which is exaggerated by the weight of the user during diaper application.

Absorbent articles may be otherwise elasticized in order to provide enhanced stretchability of the article chassis. These absorbent articles may incorporate elastomerically stretchable outercovers, bodyside liners, absorbent cores and the like to stretch around the user for improved appearance, fit and leakage containment. However, diapers that utilize stretchable elastomeric materials in its construction may be more costly and complex as stretchable materials can be more difficult to process during manufacturing.

Stretchable absorbent cores, whether extensible, elastic, or both, have been utilized in diaper construction in conjunction with stretchable chassis components to enhance diaper stretchability. However, the introduction of additional stretchable materials into the construction of diapers is generally a tradeoff where greater stretch performance is achieved by the use of more costly materials that may be more difficult to manufacture.

What is needed in the art are disposable absorbent articles (e.g., a diaper) with enhanced stretch capability that is relatively inexpensive, simple to manufacture, comfortable, and convenient to use.

SUMMARY OF THE INVENTION

In general, the present invention is directed to a disposable absorbent article having a longitudinal axis, a lateral axis, and a lateral centerline generally defining longitudinal front and back halves of the article. The article has a front end and a back end. The article comprises a liner adapted for contiguous relationship with a wearer's body. An outer cover is in generally opposed relationship with the liner. The article has a surface area defined at least in part by at least one of the liner and the outer cover. An absorbent core has a front edge, a back edge, and a surface area which is less than about 50% of the surface area of the article. The front edge of the absorbent core is in a closer proximity to the front end of the article than the back edge of the absorbent core is to the back end of the article. At least one of the liner and the outer cover is stretchable in at least one direction. The absorbent core is disposed between the liner and the outer cover and bonded to at least one of the liner and the outer cover thereby inhibiting the stretchability of the liner or the outer cover.

BRIEF DESCRIPTION OF THE DRAWINGS

FIG. 7 illustrates specific characteristics for specific embodiments of the present invention.

DESCRIPTION OF PREFERRED EMBODIMENTS

Figure 1:
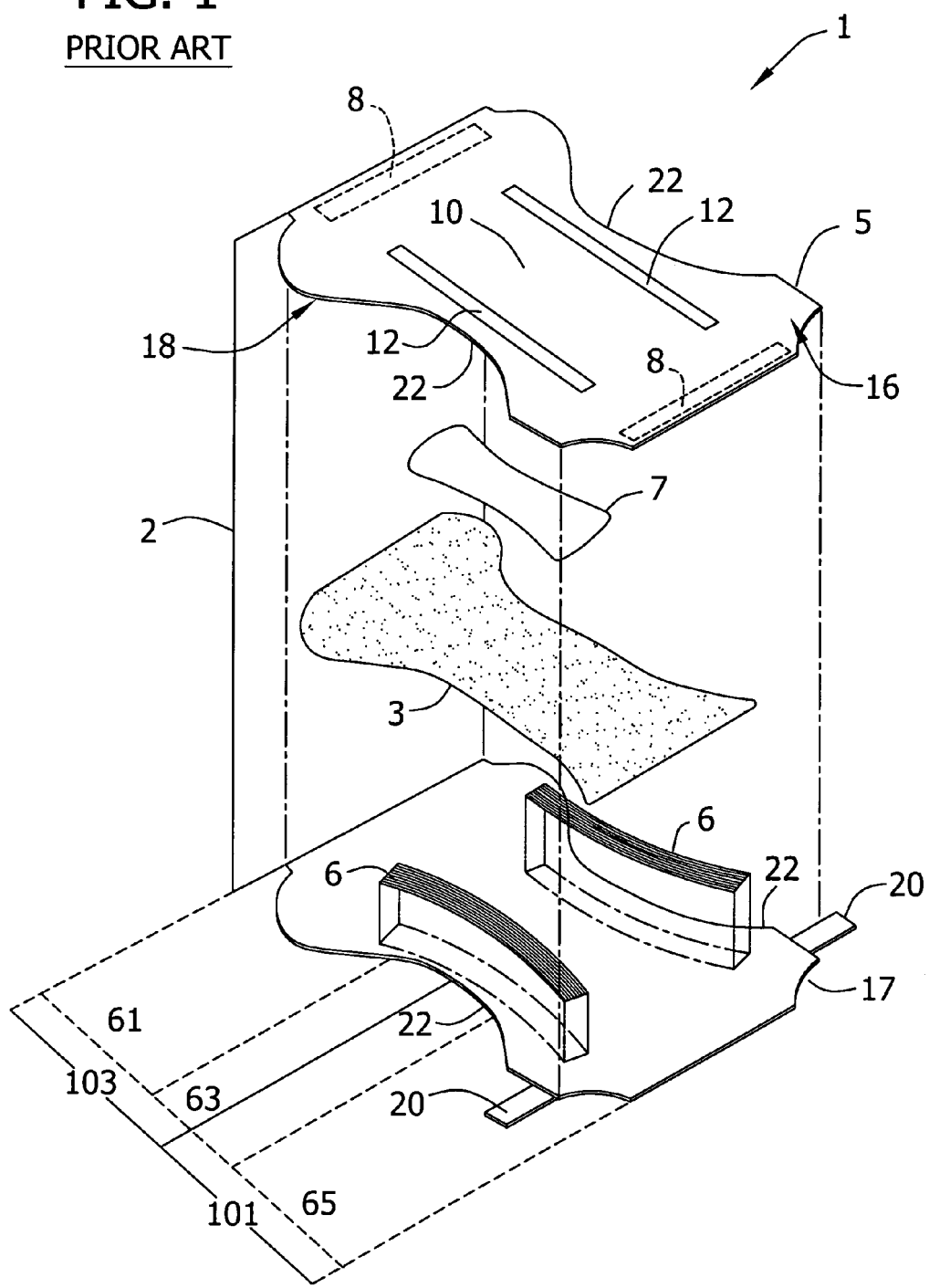
FIG. 1 illustrates a prior art diaper assembly.

In the following detailed description of the preferred embodiments, reference is made to the accompanying drawing that forms a part hereof, and in which is shown by way of illustration specific embodiments in which the invention may be practiced. It is understood that other embodiments may be utilized and structural changes may be made without departing from the scope of the present invention.

The leading digit(s) of reference numbers appearing in the Figures generally correspond to the Figure number in which that component is first introduced, such that the same reference number is used throughout to refer to an identical component which appears in multiple Figures. Signals and connections may be referred to by the same reference number or label, and the actual meaning will be clear from its use in the context of the description.

In one embodiment of the present invention, a disposable absorbent article is provided. The disposable absorbent article can absorb and contain body exudates. The disposable absorbent article is typically discarded after a limited period of used. The articles are not typically intended to be laundered or otherwise restored for reuse. The articles are conveniently placed against or in proximity to the body of the wearer to absorb and contain various exudates discharged from the body, thereby protecting the wearer's skin and preventing leakage of the discharge exterior of the article.

The present invention described herein is directed to stretchable disposable absorbent articles. While the present description will particularly be made in the context of a diaper article, it should be understood that the present invention is also applicable to other disposable personal care absorbent articles, such as adult incontinence articles, sanitary napkins, children's training pants and the like.

As used herein, "disposable absorbent article" refers to a disposable absorbent article which absorbs and contains body exudates. Typically, they are intended to be discarded after a limited period of use. The articles are not intended to be laundered or otherwise restored for reuse. The articles can be placed against or in proximity to the body of the wearer to absorb and contain various exudates discharged from the body.

As used herein, "chassis" refers to the body or frame of the disposable absorbent article. It will typically include one or more layers of suitable material. These layers may include, but are not limited to, the bodyside liner, outer cover, leg and waist elastics, and the like.

As used herein, the term "layer" when used in the singular may have the dual meaning of a single element or a plurality of elements.

As used herein, the term "surface" refers to any layer, film, woven, nonwoven, laminate, composite, or the like, whether pervious or impervious to air, gas, and/or liquids.

As used herein, the term "leg elastic member" and "waist elastic member" refer to elastic material generally adapted to fit about the legs and waist of a wearer in use to maintain a positive, contacting relationship with the wearer to effectively reduce or eliminate the leakage of body exudates from the diaper.

As used herein, the term "liquid permeable" refers to the ability of liquid, such as urine, to readily penetrate through the thickness of a layer or laminate under ordinary use conditions in a direction generally perpendicular to the plane of the layer or laminate at the point of liquid contact.

As used herein, the term "liquid impermeable" refers to the inability of liquid, such as urine, to readily penetrate through the thickness of a layer or laminate under ordinary use conditions in a direction generally perpendicular to the plane of the layer or laminate at the point of liquid contact.

As used herein, the term "hydrophilic" describes fibers or the surfaces of fibers that are wetted by the aqueous liquids in contact with the fibers. The degree of wetting of the materials can, in turn, be described in terms of the contact angles and the surface tensions of the liquids and materials involved.

As used herein, the term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding and hydrophobic associations.

As used herein, "thermal point bonding" refers to passing a fabric or web of fibers to be bonded between a heated calender roll and an anvil roll. The calender roll is usually, though not always, patterned in some way so that the entire fabric is not bonded across its entire surface.

As used herein, "ultrasonic bonding" refers to a process performed, for example, by passing the fabric between a sonic horn and anvil roll.

As used herein, "adhesive bonding" refers to an adhesive, such as a hot melt adhesive, that is applied between a film and a non-woven fiber material to bind the film and non-woven together. The adhesive can be applied for example, by melt spraying, printing or meltblowing.

As used herein, the term "extensible" refers to that property of a material where upon removal of an extending force, it provides a substantially permanent deformation and/or does not exhibit a significant retractive force.

As used herein, the term "elastic," or "elastomeric" refers to that property of a material where upon removal of an extending force, it is capable of substantially recovering its original size and shape and/or exhibits a significant retractive force.

As used herein, the term "stretch," or "stretchable" refers to a material that is either elastic or extensible. That is, the material is capable of being extended, deformed, or the like, without breaking, and may or may not significantly retract after removal of an extending force.

As used herein, the term "biaxial stretch" refers to a material having stretchability in two directions perpendicular to one another, e.g. stretchability in a machine direction and in a cross machine direction, or in a longitudinal direction (front to back) and a lateral direction (side to side).

As used herein, the term "necked" or "neck-stretched" interchangeably refer to a method of elongating a nonwoven fabric, generally in the longitudinal, or machine direction, to reduce its width in a controlled manner to a desired amount. The controlled stretching may take place under cool, room temperature or greater temperatures to provide heat setting and is limited to an increase in overall dimension in the direction being stretched up to the point required to break the fabric. When relaxed, the web retracts toward its original dimensions.

As used herein, the term "film" refers to a thermoplastic film made using a film extrusion and/or foaming process, such as a cast film or blown film extrusion process. For the purposes of the present invention, the term includes nonporous films as well as microporous films. Films may be vapor permeable or vapor impermeable, and function as liquid barriers under normal use conditions.

As used herein, the term "join" refers to the condition where a first member, or component, is directly or indirectly affixed, adhered, or otherwise connected to a second member or component such as when each is directly bonded to intermediate elements.

As used herein, the term "inner" refers to a surface that faces the wearer when in use.

As used herein, the term "outer" refers to a surface opposite that which faces the wearer when in use.

As used herein, "affixed" or "bonded" refers to the joining, adhering, connecting, attaching, or the like, of two elements. Two elements will be considered to be bonded together when they are bonded directly to one another or indirectly to one another, such as when each is directly bonded to intermediate elements.

As used herein, the term "thermoplastic" refers to uncrosslinked polymers of a thermally sensitive material which flows under the application of heat or pressure.

As used herein, the term "machine direction" refers to the longitudinal direction.

As used herein, the term "cross-machine direction" refers to the lateral direction.

As used herein the term "longitudinal" and "transverse" refers to the longitudinal axis that lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

As used herein, the term "polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

As used herein, the term "metallocene polymers" refers to those polymer materials that are produced by the polymerization of at least ethylene using metallocenes or constrained geometry catalysts, a class of organometallic complexes, as catalysts.

As used herein, the term "nonwoven" and "nonwoven web" refer to fibrous materials and webs of fibrous material which are formed without the aid of a textile weaving or knitting process.

As used herein, "bonded carded" refers to staple fibers which are usually purchased in bales. The bales are placed in a picker which separates the fibers. Next, the fibers are sent through a combing or carding unit which further breaks apart and aligns the staple fibers in the machine direction so as to form a machine direction-oriented fibrous non-woven web. Once the web has been formed, it is then bonded by one or more of several bonding method powder bonding and pattern bonding.

As used herein, "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced.

As used herein, "meltblown fiber" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter (the average microfiber diameter is not greater than about 100 microns, for example, having an average diameter of from about 0.5 microns to about 50 microns, more particularly, microfibers may have an average diameter of from about 4 microns to about 40 microns).

As used herein, "superabsorbent" refers to a water-swellable, water-insoluble organic or inorganic material capable, under the most favorable conditions, of absorbing at least about 15 times its weight and, more desirably at least about 30 times its weight in an aqueous solution containing 0.9 weight percent sodium chloride. The superabsorbent materials can be natural, synthetic, or a combination thereof.

FIG. 1 is an isometric top view which illustrates one embodiment of a typical diaper 1 assembly. The diaper generally defines a front waist region 61, a back waist region 65 and an intermediate region 63 interconnecting the front waist region 61 and the back waist region 65. The configuration of the diaper 1 may be of various suitable shapes. For example, in the unfastened configuration, the diaper 1 may have a generally rectangular shape, T-shape, I-shape, hourglass shape, or a combination thereof. The present embodiment illustrates the diaper 1 having a generally hourglass shape in an unfastened flat position. Examples of diaper configurations suitable for use in connection with the present invention and other components suitable for use on diapers are described in U.S. Pat. No. 4,798,603 issued Jan. 17, 1989, to Meyer et al., U.S. Pat. No. 5,176,668 issued Jan. 5, 1993, to Bernardin, U.S. Pat. No. 5,176,672 issued Jan. 5, 1993, to Bruemmer et al., U.S. Pat. No. 5,192,606 issued Mar. 9, 1993, to Proxmire et al., and U.S. Pat. No. 5,509,915 issued Apr. 23, 1996, to Hanson et al; the disclosures of which are herein incorporated by reference.

The various components of the diaper 1 are integrally assembled together employing various types of suitable attachment means, such as with adhesives, sonic bonding, thermal bonding or a combination thereof. In the shown embodiment, the outer cover 17 and the bodyside liner 5 are assembled to each other with the absorbent core 3 therebetween with an adhesive, such as a hot melt, pressure-sensitive adhesive. The adhesive may be applied as a uniform continuous layer of adhesive, a patterned layer of adhesive, a sprayed pattern of adhesive, or any of separate lines, swirls or dots of adhesive. In addition, the absorbent core 3 may also be connected to the bodyside liner 5, the outer cover 17, or both using means as are well known to those skilled in the art. For example, the absorbent core 3 may be connected to the bodyside liner 5, the outer cover 17, or both with and adhesive. The adhesive may be applied as a uniform continuous layer of adhesive, a patterned layer of adhesive, a sprayed pattern of adhesive, or any of separate lines, swirls or dots of adhesive. Alternatively, the absorbent core 3 may be attached to the bodyside liner 5, the outer cover 17, or both using ultra sonic bonding, thermal bonding, or the like. In another alternative, the absorbent core 3 may be attached to the bodyside liner 5, the outer cover 17, or both using conventional fasteners such as buttons, hook and loop type fasteners, adhesive tape fasteners, and the like.

Other diaper components, such as the leg elastic members 6, the waist elastic members 8 and the fasteners 20, may be assembled into the diaper 1 article by employing the above-identified attachment mechanisms. Materials suitable for use as the leg elastic members 6 and waist elastic members 8 are well known to those skilled in the art. Exemplary of such materials are sheets or strands or ribbons of a polymeric, elastomeric material which are adhered to the outer cover 17 in a stretched position, or which are attached to the outer cover 17 while the outer cover is pleated, such that elastic constrictive forces are imparted to the outer cover 17. The leg elastic members 6 may also include such materials as polyurethane, synthetic rubber, natural rubber, or both.

As representatively illustrated in FIG. 1, the disposable diaper 1 may include a pair of containment flaps 12 that are configured to provide a barrier and to contain the lateral flow of body exudates. The containment flaps 12 may be located along the laterally opposed side edges 22 of the diaper 1 adjacent the side edges of the absorbent core 3. Alternatively, the containment flaps 12 may be located on the side edges 22 of the bodyside liner 5. The side edges 22 of the bodyside liner 5 and the side edges 22 of outer cover 17 combined form the side edges 22 of the diaper 1. Each containment flap 12 typically defines an unattached edge which is configured to maintain an upright, perpendicular configuration in at least the crotch region 10 of the diaper 1 to form a seal against the wearers body. The containment flaps 12 may extend longitudinally along the entire length of the absorbent core 3 or may only extend partially along the length of the absorbent core 3. When the containment flaps 12 are shorter in length than the absorbent core 3, the containment flaps 12 can be selectively positioned anywhere along the side edges 22 of the bodyside liner 5 adjacent the side edges of the absorbent core 3 in the crotch region 10. In a particular aspect of the invention, the containment flaps 12 extend along the entire length of the absorbent core 3 to better contain the body exudates. Such containment flaps 12 are generally well known to those skilled in the art. For example, suitable constructions and arrangements for containment flaps 12 are described in U.S. Pat. No. 4,704,116 issued Nov. 3, 1987, to K. Enloe, the disclosure of which is hereby incorporated by reference.

Fastening means, such as hook and loop fasteners 20, may be employed to secure the diaper 1 on a wearer. Alternatively, other fastening means, such as buttons, pins, snaps, adhesive tape fasteners, cohesives, mushroom-and-loop fasteners, or the like, may be employed. The fasteners 20 may be located at either or both of the front waist portion 103 and the back waist portion 101 of the chassis 2. For example, each of the hook fasteners 20 are assembled and attached to extend from the side panels (not shown) that are attached to the laterally opposed side edges in the back waist portion 101. Such fastening systems generally comprise a "hook" or hook-like, male component, and a cooperating "loop" or loop-like, female component which engages and releasably interconnects with the hook component. Desirably, the interconnection is selectively releasable and re-attachable.

Conventional hook and loop fastening systems are, for example, available under the VELCRO trademark. In a particular embodiment, the fasteners 20 may be a microhook material such as that distributed under the designation CS200 by 3M Company, a business having offices in St. Paul, Minn. Another suitable micro-hook material is distributed under the designation VELCRO CFM-29 1058, and is available from VELCRO U.S.A., Inc., a business having offices in Manchester, N.H.

The loop element may be provided directly by the outer cover 17 of the diaper 1 to provide a "fasten anywhere" mechanical fastening system for improved fastening, Alternatively, the diaper 1 may include one or more attachment panels (not shown) to which the fasteners 20 are configured to releasably engage. For example, when the fasteners 20 are hook fasteners located in the back waist section 101 of the diaper 1 as illustrated, the diaper 1 may include a corresponding attachment panel such as a complementary loop element on the outward facing surface in the front waist section 103. The attachment panels may be provided by a woven fabric, a nonwoven fabric, a knitted fabric, a perforated or apertured layer, and the like, as well as combinations thereof. For example, a suitable material for the attachment panel can be composed of a 2 bar, warp knit fabric of the type available from Guilford Mills, Inc., Greensboro, N.C. under the trade designation #34285, as well other of knit fabrics.

The diaper 1 may further include a pair of side panels (not shown) to which the fasteners 20 are attached. Generally, the side panels are attached to the side edges of the diaper 1 in one of the waist sections and extend laterally outward therefrom. The side panels-may be elastic or otherwise rendered elastomeric.

For example, the side panels may be an elastomeric material such as a neck-bonded laminate (NBL) or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., the disclosures of which are hereby incorporated by reference. Examples of articles that include elasticized side panels and selectively configured fastener tabs are described in U.S. Pat. No. 5,496,298 issued Mar. 5, 1996 to Kuepper et al.; U.S. Pat. No. 5,540,796 to Fries; and U.S. Pat. No. 5,595,618 to Fries; the disclosures of which are also incorporated herein by reference.

As illustrated in FIG. 1, the diaper 1 may also include a surge management layer 7 which helps to decelerate and diffuse surges or gushes of liquid that may be rapidly introduced into the absorbent core 3 of the diaper 1. Desirably, the surge management layer can rapidly accept and temporarily hold the liquid prior to releasing the liquid into the storage or retention portions of the absorbent core 3. In the illustrated embodiment, for example, the surge management layer 7 is interposed between the inner surface 16 of the bodyside liner 5 and the absorbent core 3. Alternatively, the surge management layer 7 may be located on the outer surface 18 of the bodyside liner 5. Examples of suitable surge management layers 7 are described in U.S. Pat. No. 5,486,166 entitled FIBROUS NONWOVEN WEB SURGE LAYER FOR PERSONAL CARE ABSORBENT ARTICLES AND THE LIKE by C. Ellis and D. Bishop, which issued Jan. 23, 1996 and U.S. Pat. No. 5,490,846 entitled IMPROVED SURGE MANAGEMENT FIBROUS NONWOVEN WEB FOR PERSONAL CARE ABSORBENT ARTICLES AND THE LIKE by C. Ellis and R. Everett, which issued Feb. 13, 1996; the entire disclosures of which are hereby incorporated by reference in a manner that is consistent herewith.

The diaper 1 may further include a ventilation layer (not illustrated) located between the absorbent core 3 and the outer cover 17 to insulate the outer cover 17 from the absorbent core 3 to reduce the dampness of the garment facing surface of the outer cover 17.

The assembled layered components of the diaper 1, including the bodyside liner 5 and the outer cover 17 form chassis 2. Desirably, diaper 1 components may be assembled together using ultrasonic bonding techniques for reduced manufacturing cost.

Figure 2:
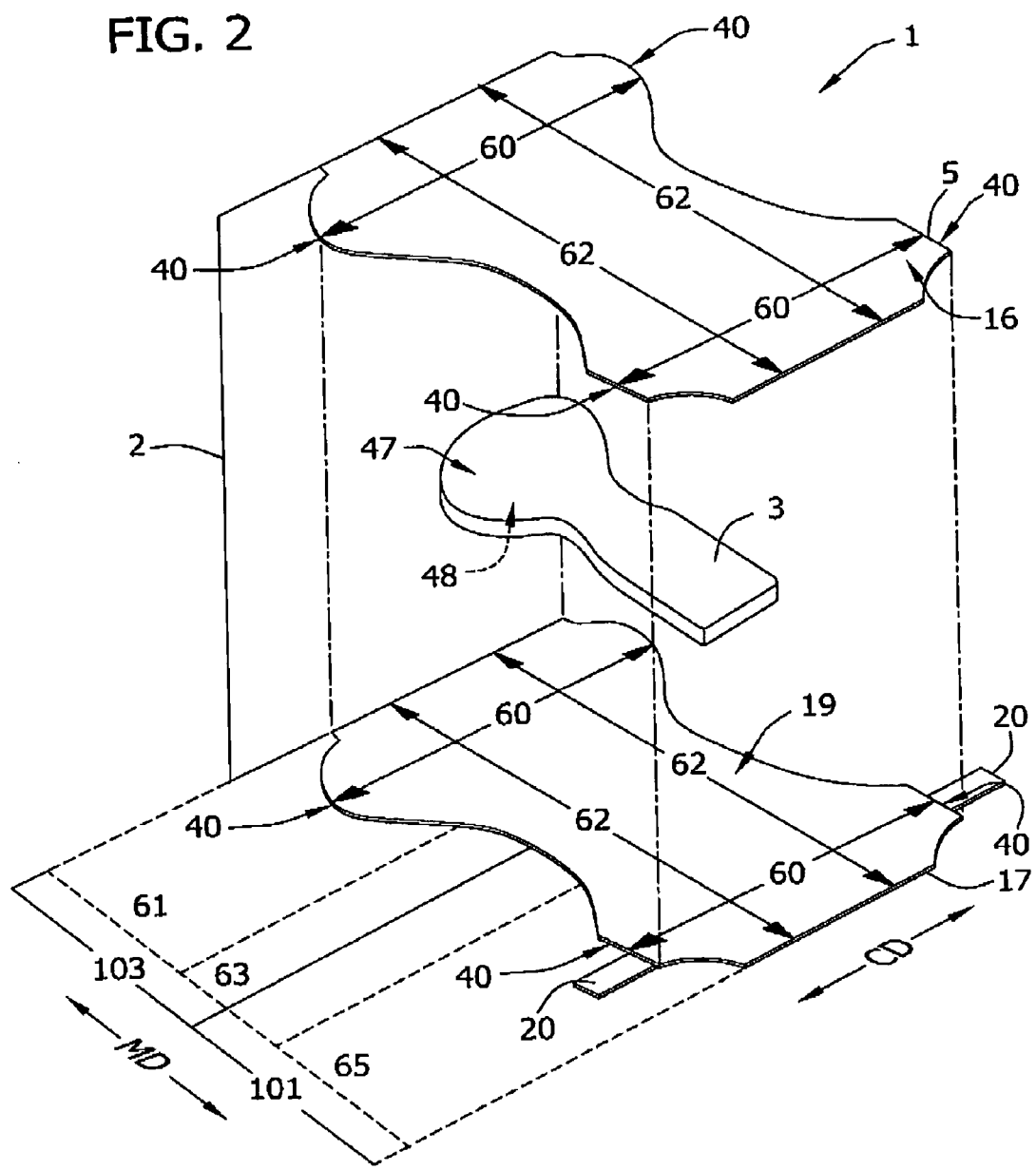
FIG. 2 illustrates a partial diaper assembly of the present invention.

FIG. 2 is an isometric top view of one embodiment of the present invention illustrating the bodyside liner 5, the absorbent core 3 and the outer cover 17 of the present invention only without depicting other intermediate layers and components such as the surge management layer 7, the leg elastic members 6, the containment flaps 12, etc. The present invention cost effectively utilizes a non-stretch, or low stretch absorbent core 3 wherein the ratio of the surface area of the absorbent core 3 in relation to the surface area of the chassis 2 is significantly reduced such that the chassis 2 is stretchable in at least the cross-machine direction in at least the back one-half portion 101 of the chassis 2.

Bodyside Liner

The stretchable bodyside liner 5 may be extensible in the cross-machine direction, machine direction, or biaxially extensible in both the cross-machine direction and the machine direction. The preferred embodiment of the present invention is a bodyside liner 5 that is extensible in the cross-machine direction. In particular, it is desirable that the bodyside liner 5 is extensible in at least the one-half back waist region 101. The bodyside liner 5 is desirably extensible such that it is capable of stretching with the outer cover 17 to provide improved fastening, fit and containment of body fluids. In particular, it is desirable that the waist sections 40 of the bodyside liner 5 are capable of extending and permanently deforming in the lateral direction 60 (i.e., cross-machine direction) to provide improved fit of the diaper 1 about the wearer and improved coverage of the wearer's hips and buttocks.

The bodyside liner 5 suitably presents a bodyfacing surface which is compliant, soft feeling, and nonirritating to the wearers skin. Further, the bodyside liner 5 may be less hydrophilic than the absorbent core 3, to present a relatively dry surface to the wearer, and may be sufficiently porous to be liquid permeable, permitting liquid to readily penetrate through its thickness in order to isolate the wearer's skin from liquids held in the absorbent core 3. A suitable bodyside liner 5 may be manufactured from a wide selection of web materials, such as porous foams, reticulated foams, apertured plastic films, natural fibers (for example, wood or cotton fibers), synthetic fibers (for example, polyester or polypropylene fibers), or a combination thereof.

The stretchable bodyside liner 5 may further be composed of various stretchable materials such as a necked fabric, a creped fabric, a micro-pleated fabric, perforated polymer films, or the like, or a combination thereof. The fabrics may be non-elastic woven or nonwoven materials, such as spunbond fabrics. Examples of suitable manufacturing techniques and suitable necked nonwoven fabric materials for such an extensible bodyside liner 5 are described in U.S. Pat. No. 4,965,122 entitled REVERSIBLY NECKED MATERIAL, by M. T. Morman which issued Oct. 23, 1990.

Desirably, the bodyside liner 5 is made from non-elastic neckable materials for reduced cost and improved manufacturing efficiency. Suitable non-elastic neckable materials include nonwoven webs, woven materials and knitted materials. Such webs can include one or more fabric layers. Nonwoven fabrics or webs have been formed from many processes, for example, bonded carded web processes, meltblowing processes and spunbonding processes. The nonelastic neckable material is preferably formed from at least one member selected from fibers and filaments of inelastic polymers. The polymers include polyesters, for example, polyethylene terephthalate, polyolefins, for example, polyethylene and polypropylene, polyamides, for example, nylon 6 and nylon 66. These fibers or filaments are used alone or in a mixture of two or more thereof.

Suitable fibers for forming the neckable material include natural and synthetic fibers as well as bicomponent; multicomponent, and shaped polymer fibers. Many polyolefins are available for fiber production according to the present invention, for example, fiber forming polypropylenes include Exxon Chemical Company's Esbodyne® PD 3445 polypropylene and Himont Chemical Company's PF-304. Polyethylenes such as Dow Chemical's ASPUN 6811A linear low density polyethylene, 2553 LLDPE and 25355 and 12350 high density polyethylene are also suitable polymers. The nonwoven web layer may be bonded to impart a discrete bond pattern with a prescribed bond surface area. If too much bond area is present on the neckable material, the material will break before it necks. If there is not enough bond area, then the neckable material will pull apart. Typically, the percent bonding area useful in the present invention ranges from around 5 percent to around 40 percent of the area of the neckable material.

For example, a particularly suitable extensible material for the bodyside liner 5 is a necked spunbond web of polypropylene fibers having a basis weight of from about 5 to about 30 gsm. Such a web may be necked up to about 80 percent. The neckable materiel may be necked to form the stretchable bodyside liner 5 by conventional necking processes that typically vary the surface speed of the web to draw or neck the material. Such necking will allow the material to stretch in the transverse direction. The necked nonwoven fabric materials are typically capable of being necked up to about 80 percent. For example, the extensible bodyside liner 5 of the various aspects of the present invention may be necked from about 10 to about 80 percent, desirably from about 20 to about 60 percent, and more desirably from about 30 to about 50 percent for improved performance, When provided by the extensible materials as described above, the stretchable bodyside liner 5 may also provide a substantially permanent deformation of at least about 10 percent, desirably at least about 20 percent, and more desirably at least about 30 percent when subjected to a tensile force of 100 gmf per inch (per 2.54 cm) of width of the test sample according to the Material Elongation and Deformation Tensile Test set forth herein. Substantially permanent deformations less than those set forth above may not provide the desired permanent deformation for improved fastening, containment and fit.

In still other aspects, the bodyside liner 5 can provide a substantially permanent deformation of from about 10 to about 100 percent and desirably from about 20 to about 80 percent when subjected to the tensile force of 100 gmf per inch (per 2.54 cm) of width of the test sample according to the Material Elongation and Deformation Tensile Test set forth herein. The extensible bodyside liner 5 may also provide an elongation of at least about 20 percent, desirably at least about 25 percent and more desirably at least about 30 percent when subjected to a tensile force of 100 gmf per inch (per 2.54 cm) of width of the test sample according to the Material Elongation and Deformation Tensile Test set forth herein for improved performance.

For example, in an alternate embodiment, the bodyside liner 5 may have elastic properties. The body side liner 5 may be elastic in the cross-machine direction, the machine direction, or biaxially elastic in both the cross-machine direction and the machine direction.

The stretchable body side liner 5 may suitably be composed of a neck-stretched, spunbond web with KRATON G strands, such as 0.4 osy (60% neck-stretched) polypropylene spunbond laminated to 0.4osy strands of KRATON MM G2760 with 12 strands per inch, which is stretched then allowed to retract. Other suitable elastic materials may include a neck stretched/creped spunbond material.

The stretchable liner 10 may be composed of a substantially hydrophobic material, and the hydrophobic material can, optionally, be treated with a surfactant or otherwise processed to impart a desired level of wettability and hydrophilicity. For example, the elastic material can be surface treated with about 0.45 weight percent of a surfactant mixture including AHCOVEL N-62 from Hodgson Textile Chemicals of Mount Holly, N.C., U.S.A. and GLUCOPON 220UP from Henkel Corporation of Ambler, Pa., in an active ratio of 3:1. The surfactant can be applied by any conventional means, such as spraying, printing, brush coating or the like. The surfactant can be applied to the entire stretchable liner 10 or can be selectively applied to particular sections of the stretchable liner 10, such as the medial section along the longitudinal centerline.

Outer Cover

The stretchable outer cover 17 may be extensible in the cross-machine direction, the machine direction, or biaxially extensible in both the cross-machine direction and the machine direction. In part, it is desirable that the outer cover is extensible in at least the back one-half portion 101. The preferred embodiment of the present invention is an outer cover 17 that is extensible in the cross-machine direction. The outer cover 17 is desirably extensible such that it is capable of extending with the bodyside liner 5 to improved fastening, fit and containment of body fluids.

The extensible outer cover 17 may include a stretchable fabric layer which is operatively attached or otherwise joined to extend over a major portion of the outward surface of the article. In areas where the extensible outer cover 17 is not affixed to the non-stretchable or low stretchable absorbent core 3, the extensible outer cover 17 is free to advantageously stretch with minimal force and with a high amount of permanent deformation.

In particular, it is desirable that the waist sections 40 of the outer cover 17 are capable of stretching and permanently deforming in the lateral direction 60 (i.e., cross-machine direction) to provide improved fit of the diaper 1 about the wearer and improved coverage of the wearer's hips and buttocks.

For example, in the shown embodiment, the fasteners 20 are located along the side edges of the waist sections 40 in the back portion 65 of the diaper 1. As the diaper 1 is applied to the wearer, the caregiver tends to pull on the fasteners 20 to better fit the diaper 1 around the waist of the wearer. The pulling on the fasteners 20 create stretch tensions in the back portion 65 to extend the diaper 1 over the buttocks of the wearer for improved fit and appearance. The enhanced buttock coverage is due to the permanent deformation of the outer cover 17 in the back one-half portion 101 when lateral forces are exerted to fasten the diaper 1 about the wearer.

Moreover, the enhanced stretch of the outer cover 17 improves diaper 1 containment. For example, as the absorbent core 3 absorbs fluid exudates and expands outwardly, the front portion 61, the middle portion 63 and the back portion 65 of the diaper 1 may readily elongate and extend in correspondence with the expansion of the absorbent core 3 and/or other components of the diaper 1 to more effectively contain the exudates.

The extensible outer cover 17 of the present invention is desirably capable of providing a selected elongation when subjected to an applied tensile force. The extensible outer cover 17 is also desirably capable of providing a selected, sustained deformation when subjected to an applied tensile force and then allowed to relax for a selected time period after removing the applied tensile force. The measurement of the selected time period begins immediately after the removal of the tensile force. Preferably, the sustained deformation is a substantially permanent deformation. The selected elongation and sustained deformation can occur at least along the lateral direction 60 (i.e., cross-machine direction) of the diaper 1. Optionally, the selected elongation and sustained deformation can occur along the longitudinal direction 62 (i.e., machine direction) of the diaper 1, or may occur along both the lateral direction 60 and longitudinal direction 62 of the diaper 1.

In particular aspects, the extensible outer cover 17 can provide an elongation of at least about 10 percent, desirably at least about 20 percent, more desirably at least about 30 percent and even more desirably at least about 40 percent when subjected to a tensile force of 100 gmf per inch (per 2.54 cm) of width of the test sample according to the Material Elongation and Deformation Tensile Test set forth herein. Elongation less than those above may not provide the desired stretch for improved fastening, containment and fit. In other aspects, the extensible outer cover 17 may be capable of providing an elongation of from about 10 percent to about 200 percent and desirably from about 30 percent to about 100 percent when subjected to a tensile force of 100 gmf per inch (per 2.54 cm) of width of the test sample according to the Material Elongation and Deformation Tensile Test set forth herein.

In certain aspects, the extensible outer cover 17 may also provide a substantially permanent deformation of at least about 10 percent, at least about 15 percent, at least about 17 percent, at least about 20 percent, at least about 25 percent and desirably at least about 30 percent when subjected to a tensile force of 100 gmf per inch (per 2.54 cm) of width of the test sample according to the Material Elongation and Deformation Tensile Test set forth herein. Substantially permanent deformations less than those set forth above may not provide the desired improved fastening, containment, enhanced buttock coverage and breathability. In still other aspects, the extensible outer cover 17 can provide a substantially permanent deformation of from about 10 to about 100 percent and desirably from about 17 to about 80 percent when subjected to the tensile force of 100 gmf per inch (per 2.54 cm) of width of the test sample according to the Material Elongation and Deformation Tensile Test set forth herein. It should be noted that the permanent deformation properties of the extensible outer cover 17 are determined when the outer cover 17 is dry.

In the various configurations or the invention, the stretchable outer cover 17 is also configured to be substantially impermeable to aqueous liquid. For example, the outer cover 17 may have a construction that is capable of supporting a selected hydrohead of water substantially without leakage therethrough. A suitable technique for determining the resistance of a material to liquid penetration is Federal Test Method Standard FTMS 191 Method 5514, 1978, or an equivalent thereof. Since the outer cover 17 is extensible, a layer of nylon net material having a thickness of about 0.1 mm may be needed to support the outer cover material for this test. The net material may be provided by nylon threads arranged in a hexagonal or honeycomb-like pattern with openings approximately 4 mm across.

For example, the net material may be purchased from Wal-Mart Stores under the trade designation T-246. The net material is liquid pervious and does not significantly affect the hydrohead values obtained. The stretchable outer cover 17 is sufficiently impermeable to liquid and semi-liquid materials to substantially prevent the undesired leakage of waste materials, such as urine and feces. For example, the stretchable outer cover 17 can desirably support a hydrohead of at least about 45 centimeters (cm) substantially without leakage. The stretchable outer cover 17 can alternatively support a hydrohead of at least about 55 cm, and optionally, can support a hydrohead of at least about 60 cm, or more, to provide improved benefits.

The extensible outer cover 17 may include necked fabrics, creped fabrics, crimped fiber fabrics, extendable fiber fabrics, bonded-carded fabrics, micro-pleated fabrics, polymer films, or a combination thereof. The fabrics may be woven or nonwoven materials, such as spunbond fabrics, in a particular embodiment, the extensible outer cover 17 may be composed of a stretchable laminate of two or more layers. The extensible outer cover 17 may be a necked laminate formed from at least one neckable fabric laminated to at least one stretchable film material wherein the necked laminate is extensible in at least the cross-machine direction. The extensible outer cover 17 may otherwise be a laminate formed from at least one necked fabric laminated to at least one stretchable film material. In such a configuration, the laminate need not be necked.

Typically, such necked nonwoven fabric materiels are capable of being necked up to about 80 percent. For example, the extensible outer cover 17 of the various aspects of the present invention may be provided by a material that has been necked from about 10 to about 80 percent, desirably from about 20 to about 60 percent, and more desirably from about 30 to about 50 percent for improved performance.

In a particular embodiment, the extensible outer cover 17 is made from a necked laminate material to provide the desired levels of stretch as well as liquid impermeability and vapor permeability. For example, the extensible outer cover 17 may be a necked laminate formed from sheet layers of at least one neckable fabric laminated to at least one film material wherein the necked laminate is stretchable in at least the cross-machine direction and does not appreciably retract. Desirably, both the neckable fabric and the film material are non-elastic materials for increased permanent set, reduced cost and improved manufacturing efficiency. Suitable necked laminates that include at least one non-elastic neckable material laminated to at least one non-elastic film material are described in U.S. patent application Ser. No. 09/455,513 filed Dec. 6, 1999 and entitled "TRANSVERSELY EXTENSIBLE AND RETRACTABLE NECKED LAMINATE OF NON-ELASTIC SHEET LAYERS", the entire disclosure of which is hereby incorporated by reference.

The non-elastic film layer may be made from either cast or blown film equipment and may be coextruded and can be embossed if so desired. The film layer may be made from any suitable non-elastic polymer composition and may include multiple layers.

The non-elastic film layer can also be breathable. For example, the non-elastic film layer may contain such fillers as micropore developing fillers, e.g. calcium carbonate; opacifying agents, e.g. titanium dioxide; and antiblock additives, e.g. diatomaceous earth. Suitable polymers for the non-elastic film layer include, but are not limited to, non-elastic extrudable polymers such as polyolefin or a blend of polyolefins, nylon, polyester, ethylene vinyl alcohol, or a combination thereof More particularly, useful polyolefins include polypropylene and polyethylene. Other useful polymers include those described in U.S. Pat. No. 4,777,073 to Sheth, assigned to Exxon Chemical Patents Inc., such as a copolymer of polypropylene and low density polyethylene or linear low density polyethylene.

Alternative polymers for the film layer include those referred to as single site catalyzed polymers such as "metallocene" polymers produced according to a metallocene process and which have limited elastic properties. For example, a common metallocene is ferrocene, a complex of a metal between two cyclopentadienyl (Cp) ligands. Such metallocene polymers are available from Exxon Chemical Company of Baytown, Tex. under the trademark EXXPOL for polypropylene based polymers and EXACT for polyethylene based polymers and from Dow Chemical Company of Midland, Mich. under the name ENGAGE. Preferably, the metallocene polymers are selected from copolymers of ethylene and 1-butane, copolymers of ethylene and 1-hexene, copolymers of ethylene and 1-octene, or a combination thereof. Suitable non-elastic neckable materials for the outer cover 17 include nonwoven webs, woven materials, knitted materials, or a combination thereof, such as those described in the above-mentioned U.S. Pat. No. 4,965,122.

Nonwoven fabrics or webs have been formed from many processes, for example, bonded carded web processes, meltblowing processes and spunbonding processes. The non-elastic neckable material is preferably formed from at least one member selected from fibers and filaments of inelastic polymers. Such polymers include polyesters, for example, polyethylene terephthalate, polyolefins, for example, polyethylene and polypropylene, polyamides, for example, nylon 6 and nylon 66. These fibers or filaments are used alone or in a mixture of two or more thereof. Suitable fibers for forming the neckable material include natural fibers, synthetic fibers, bicomponent fibers, multi-component fibers, shaped polymer fibers, or a combination thereof. Many polyolefins are available for fiber production according to the present invention, for example, fiber forming polypropylenes include Exxon Chemical Company's Esbodyne® PD 3445 polypropylene and Himont Chemical Company's PF-304. Polyethylenes such as Dow Chemical's ASPUN 6811A linear low density polyethylene, 2553 LLDPE and 25355 and 12350 high density polyethylene are also suitable polymers.

The nonwoven web layer may be bonded to impart a discrete bond pattern with a prescribed bond surface area. If too much bond area is present on the neckable material, it will break before it necks. If there is not enough bond area, then the neckable material will pull apart. Typically, the percent bonding area useful in the present invention ranges from around 5 percent to around 40 percent of the area of the neckable material.

The non-elastic film layer may be laminated to the neckable material to form the laminate by conventional methods known in the art including adhesive bonding, point bonding, thermal point bonding, and sonic welding. The laminate is then necked by conventional necking processes that typically vary the surface speed of the web to draw or neck the laminate. Such necking provides striated rugosities in the film and/or laminate resulting in transverse extensibility and retractability to the necked laminate and more "cloth-like" aesthetics. It is known that stretching and orienting a filled film layer causes micropores to form in the film, but longitudinal striated rugosities do not typically form in the film layer when stretched. The film layer would instead become physically thinner and may narrow slightly. By necking the laminate, the non-elastic neckable material, which is attached to the non-elastic film layer, will neck and bring the nonelastic film layer with it, thereby forming the longitudinal striated rugosities in the film which allows the film layer to extend in the transverse direction. Alternative necked laminate materials that may be used in the outer cover 17 of the present invention are described in U.S. patent application Ser. No. 09/460,490 filed Dec. 14, 1999 and entitled "BREATHABLE LAMINATE PERMANENTLY CONFORMABLE TO THE CONTOURS OF A WEARER", the entire disclosure of which is hereby incorporated by reference.

In an alternate embodiment, the outer cover 17 has elastic properties. The outer cover 17 may be elastic in the cross-machine direction, the machine direction, or biaxially elastic in both the cross-machine direction and the machine direction.

One example of an elastic outer cover 17 material with elastic properties is a 0.3 osy polypropylene spunbond that is necked 60% in the transverse direction 60 (i.e., cross-machine direction) and creped 60% in the longitudinal direction 61, laminated with 3 grams per square meter (gsm) Findley 2525A styrene-isoprene-styrene based adhesive to 8 gsm PEBAX 2533 film with 20% $TiO_2$ concentrate. In such an elastic embodiment, the outer cover 17 can suitably be stretched, transversely and/or longitudinally, by at least 50% (to at least 150% of an initial (unstretched) width and/or length of the outer cover 17). More suitably, the outer cover 17 can be stretched, transversely and/or longitudinally, by at least 100% (to at least 200% of the unstretched width or length of the outer cover 17). Even more suitably, the outer cover 17 can be stretched, transversely and/or longitudinally, by at least 150% (to at least 250% of the unstretched width or length of the outer cover 17). Tension in the outer cover 17 at 50% extension is suitably between 50 and 1000 grams, more suitably between 100 and 600 grams, as measured on a 3 inch wide piece of the outer cover material.

A stretchable elastic outer cover 17 desirably includes a material that is substantially liquid impermeable. The stretchable outer cover 17 can be a single layer of liquid impermeable material, but desirably includes a multi-layered laminate structure in which at least one of the layers is liquid impermeable. For example, the stretchable outer cover 17 may include a liquid permeable outer layer and a liquid impermeable inner layer that are suitably joined together by a laminate adhesive (not shown) or thermal bonded attachment means. Suitable laminate adhesives, which can be applied continuously or intermittently as beads, a spray, parallel swirls, or the like, can be obtained from Bostik-Findley, Inc., of Wauwatosa, Wis., U.S.A., or from National Starch and Chemical Company, Bridgewater, N.J., U.S.A.

The liquid permeable outer layer can be any suitable material and desirably one that provides a generally cloth-like texture. One example of such a material is a thermoplastic nonwoven web, such as a spunbond thermoplastic nonwoven web made from a stretchable polymer and having a basis weight of about 1-100 grams per square meter (gsm), suitably about 5-50 gsm, more suitably 10-30 gsm. Suitable stretchable polymers for making the nonwoven web include certain flexible polyolefins, for example propylene-based polymers having both atactic and isotactic propylene groups in the main polypropylene chain. Also included are heterophasic propylene-ethylene copolymers. Heterophasic polymers are reactor blends formed by adding different levels of propylene and ethylene at different stages in the reactor. Heterophasic polymers typically include about 10-90% by weight of a first polymer segment A, about 10-90% by weight of a second polymer segment B, and 0-20% by weight of a third polymer segment C. Polymer segment A is at least about 80% crystalline and includes about 90-100% by weight propylene, as a homopolymer or random copolymer with up to 10% by weight ethylene. Polymer segment B is less than about 50% crystalline, and includes about 30-70% by weight propylene randomly copolymerized with about 30-70% by weight ethylene. Optional polymer segment C contains about 80-100% by weight ethylene and 0-20% of randomly copolymerized propylene.

Other stretchable polymers include very low density polyethylene (VLDPE), which is an ethylene-alpha olefin copolymer having a density less than 0.900 grams/cm$^3$, preferably about 0.870-0.890 grams/cm$^3$. Preferred VLDPE's are single-site catalyzed. Other stretchable polymers include random propylene-alpha olefin copolymers containing more than 10% by weight of a C2 or C4-C12 comonomer, preferably about 15-85% by weight of the comonomer, with ethylene being a preferred comonomer.

The stretchable inner layer 19 of the outer cover 17 is desirably manufactured from a thin (1-50 microns, suitably 5-25 microns, more suitably 10-20 microns) plastic film, although other stretchable liquid impermeable materials may also be used. The film layer of the outer cover 17 may contain a blend of a thermoplastic polymer and a 30-70% by weight of a particulate inorganic filler, such as calcium carbonate. The film can be oriented at least uniaxially to cause void formation around the filler particles, resulting in breathability.

Suitable stretchable polymers for making the film include stretchable olefin polymers, such as an olefinic copolymer of polyethylene. More specifically, other stretchable polymers include diblock, triblock, tetrablock or other multi-block elastomeric copolymers such as olefinic copolymers, including styrene-isoprene-styrene, styrene-butadiene-styrene, styrene-ethylene/butylene-styrene, or styrene-ethylene/propylene-styrene, which may be obtained from the Shell Chemical Company, under the trademark KRATON elastomeric resin; polyurethanes, including those available from E.I. du Pont de Nemours Co., under the trademark LYCRA polyurethane; polyamides, including polyether block amides available from Ato Chemical Company, under the trademark PEBAX polyether block amide; polyesters, such as those available from E.I. Du Pont de Nemours Co., under the trademark HYTREL polyester; and single-site or metallocene-catalyzed polyolefins having density less than about 0.91 grams/cc, available from Dow Chemical Co. under the trademark AFFINITY.

An elastic outer cover 17 may include a spunbonded laminate, a meltblown laminate, a spunbond-meltblown-spunbond laminate, or a stretch-bonded laminate (SBL) made using a stretchable polymer or blend thereof. A more specific example of suitable liquid impermeable films for use as a liquid impermeable inner layer, or as a single layer liquid impermeable stretchable outer cover 17, is a 0.02 millimeter polyethylene film commercially available from Pliant Corp. Packaging of Newport News, Va., U.S.A. If the stretchable outer cover 17 is a single layer of material, it can be embossed and/or matte finished to provide a more cloth-like appearance. The liquid impermeable material can permit vapors to escape from the interior of the disposable absorbent article, while still preventing liquids from passing through the stretchable outer cover 17.

A suitable "breathable" material is composed of a microporous polymer film or a nonwoven fabric that has been coated or otherwise treated to impart a desired level of liquid impermeability. A suitable microporous film is a PMP-1 poly (methyl pentene) film material commercially available from Mitsui Toatsu Chemicals, Inc., Tokyo, Japan, or an XKO-8044 polyolefin film commercially available from 3M Company, Minneapolis, Minn.

Another example of a suitable material for the stretchable outer cover 17 is a breathable elastic film/nonwoven laminate, described in U.S. Pat. No. 5,883,028, issued to Morman et al., herein incorporated by reference. Still more examples of materials having biaxial stretchability and retractability are disclosed in U.S. Pat. No. 5,116,662 issued to Morman and U.S. Pat. No. 5,114,781 issued to Morman, both of which are hereby incorporated by reference. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

Absorbent Core

The first surface 47 of the absorbent core 3 may be affixed to the second surface 16 of the bodyside liner 5, the second surface 48 of the absorbent core 3 may be affixed to the first surface 19 of the outer cover 17, or both. The absorbent core 3 may be affixed by adhesives, sonic bonding, thermal bonding, or a combination thereof. For example, a hot melt, pressure-sensitive adhesive may be applied as a uniform continuous layer of adhesive, a patterned layer of adhesive, a sprayed pattern of adhesive, or any of separate lines, swirls or dots of adhesive on one or both of the surfaces 47 and/or 48 of the absorbent core 3. Alternatively, the absorbent core 3 may be connected to either the bodyside liner 5, the outer cover 17, or both using conventional fasteners such as buttons, hook and loop type fasteners, adhesive tape fasteners, and the like.

The absorbent core 3 is connected or otherwise associated to the chassis 2 in an operable manner. As used herein, the term "associated" encompasses configurations in which absorbent is directly joined to the chassis 2, for example by affixing the absorbent directly to the outer cover 17 and/or bodyside liner 5, and configurations wherein the absorbent core 3 is indirectly joined to the outer cover 17 and/or bodyside liner 5, for example by affixing the absorbent core 3 to intermediate members that in turn are affixed to the chassis 2. The absorbent core 3 and the chassis 2 may be joined to each other by attachment mechanisms (not shown) such as adhesive bonds, sonic bonds, thermal bonds, pinning, stitching or any other attachment techniques known in the art, as well as combinations thereof.

For example, a substantially hydrophilic tissue wrapsheet (not shown) may be employed to help maintain the integrity of the fibrous structure of the absorbent body. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. The wrapsheet material on one side of the absorbent fibrous mass may be bonded to the wrapsheet located on the opposite side of the fibrous mass to effectively entrap the absorbent body. Therefore, the wrapsheet may, in turn be joined to the chassis of the present invention.

The absorbent core 3 of the present invention is comprised of non-stretch materials, low stretch materials, or a combination thereof. Non-stretch and/or low stretch materials are easier and more cost effective to manufacture than extensible and elastic materials. The absorbent core 3 of the diaper 1 may be manufactured in a wide variety of sizes and shapes (for example, rectangular, trapezoidal, T-shape, I-shape, hourglass shape, etc. or a combination thereof.) and from a wide variety of materials.

The absorbent core 3 of the diaper 1, is non-extensible and non-elastic with a non-stretch or low stretch capability. The absorbent core 3 may be constructed from a matrix of hydrophilic fibers, such as a web of cellulosic fluff, mixed with particles of a high-absorbency material commonly known as superabsorbent material. The absorbent core 3 may include a matrix of cellulosic fluff such as wood pulp fluff and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the absorbent core 3 to better contain and absorb body exudates. The concentration of the superabsorbent particles may also vary throughout the thickness of the absorbent core 3. Alternatively, the absorbent core 3 may include a laminate of fibrous webs and superabsorbent materials or other suitable means of maintaining a superabsorbent material in a localized area.

The high-absorbency material can be selected from natural, synthetic, modified natural polymers and materials, or a combination thereof. The high absorbency materials can be inorganic materials, such as silica gels, or organic compounds, such as crosslinked polymers. Examples of synthetic, polymeric, high-absorbency materials include the alkali metal and ammonium salts of poly(acrylic acid), poly (methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core 3 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va., DOW DRYTECH 2035LD polymer available from Dow Chemical Co. located in Midland, Mich. and Stockhausen W65431 polymer available from Stockhausen Inc., located in Greensboro, N.C.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent core 3 in an amount of from about 5 to about 90 weight percent based on total weight of the absorbent core 3.

Figure 3:
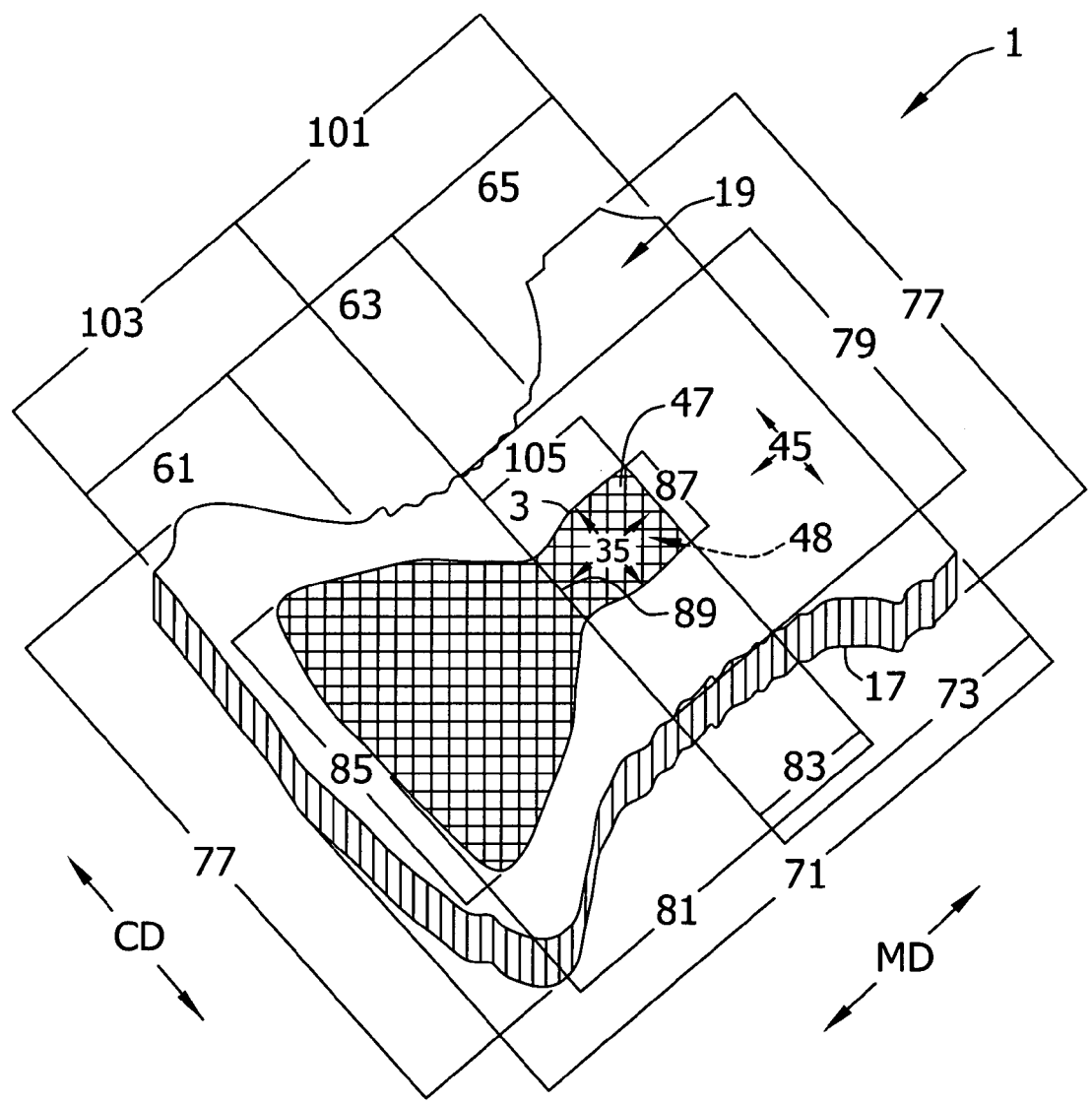
FIG. 3 illustrates a partial diaper assembly of the present invention.

FIG. 3 is an isometric top view of the preferred embodiment of the diaper 1 in an extended, flat condition with all elastic contractions and gathers removed illustrating the absorbent core 3 affixed to the outer cover 17. The bodyside liner 5 is not shown. The diaper 1 of the present embodiment includes a back portion 65, a front portion 61 and a middle portion 63 interconnecting the back portion 65 and the front portion 61. Absorbent core 3 is affixed to the inner surface 19 of the outer cover 17 of the diaper 1. The absorbent core 3 has a first absorbent core length 81 and a second absorbent core length 83, which run along the machine direction of the stretchable chassis 2 and a first absorbent core width 85, a second absorbent core width 87 and an intermediate absorbent core width 89 which run along the cross-machine direction of the stretchable chassis 2. Both the second absorbent core length 83 and a function of the second absorbent core width 87, and the intermediate absorbent core width 89 essentially define the surface area 35 of the back one-half portion 105 of the absorbent core 3. The chassis 2 has a first chassis length 71 and a second chassis length 73 which run along the machine direction of the diaper 1 and a first chassis width 77 and a second chassis width 79 which run along the cross-machine direction of the diaper 1. Both the second chassis length 73 and a function of the first chassis width 77 and the second chassis width 79 essentially define the back one-half portion 101 of the surface area 45 of the stretchable chassis 2.

The non-stretch and/or low stretch nature of the absorbent core 3 creates drag on the stretchable surface area 45 of the stretchable chassis 2 at the points of fixation of the second surface 48 of the absorbent core 3 to the inner surface 19 of the outer cover 17, at the points of fixation of the first surface 47 of the absorbent core 3 to the inner surface 16 of the bodyside liner 5, or both, particularly in the back one-half portion 101 of the stretchable chassis 2.

In particular, extensibility is critical in the back one-half portion 101 of the chassis 2. For example, if the entire second surface 48 of the back one-half portion 105 of the absorbent core 3 is affixed or laminated to the inner surface 19 of the outer cover 17, then the extensible capacity of the surface area 45 of the back one-half portion 101 of the stretchable chassis 2 is significantly reduced by the entire surface area 35 of the back one-half portion 105 of the absorbent core 3. This is significant because as the diaper 1 is applied to the wearer, the caregiver tends to pull on the fasteners 20, typically located on the outside edges of the outer cover 17 of the back one-half portion 101, to better fit the diaper 1 around the waist of the wearer. The pulling on the fasteners 20 create stretch tensions on the surface area 45 of the back one-half portion 101 of the chassis 2.

A proportionally reduced surface area 35 in the back one-half portion 105 of the absorbent core 3 will proportionally increase the corresponding surface area 45 in the back one-half portion 101 of the chassis 2 that is unencumbered by the absorbent core 3, thus increasing the surface area 45 that is able to stretch around the wearer creating greater comfort, appearance and fit for the wearer. The reduction in the surface area 35 of the back one-half portion 105 of the absorbent core 3 does not compromise the performance of the absorbent core 3 as the back surface area 35 of the absorbent core 3 is generally utilized for the fit of the diaper 1 about the wearer. Generally, the absorbent core 3 in the back one-half portion 101 of the stretchable chassis 2 does not play as vital a role in absorbency as the front one-half portion 103 of the stretchable chassis 2. This is because the crotch area where the liquid insult occurs is typically located about the front one-half portion 103 of the chassis 2. Thus, the stretch of the chassis 2 is enhanced in the back one-half portion 101 of the stretchable chassis 2 while the absorbency characteristics of the absorbent core 3 is adequately maintained.

Whether the entire surface area 35 of the back one-half portion 105 of the absorbent core 3 is affixed to the bodyside liner 5, the outer cover 17, or both of the chassis 2, or whether selective fixed points of the back one-half portion 105 of the surface area 35 of the absorbent core 3 are affixed to the bodyside liner 5, the outer cover 17, or both of the chassis 2, a reduction in the size of the absorbent core 3 in the back one-half portion 105 increases the corresponding surface area 45 in the back one-half portion 101 of the stretchable chassis 2 that is uninhibited by the attachment points of the absorbent core 3 allowing at least greater cross machine direction extension of the stretchable chassis 2. This may eliminate or greatly reduce the need for pleating chassis 2 in the cross machine direction and/or eliminate the need of a stretchable absorbent core 3 reducing the cost and complexity of manufacturing the diaper 1 of the present invention.

Figure 4:
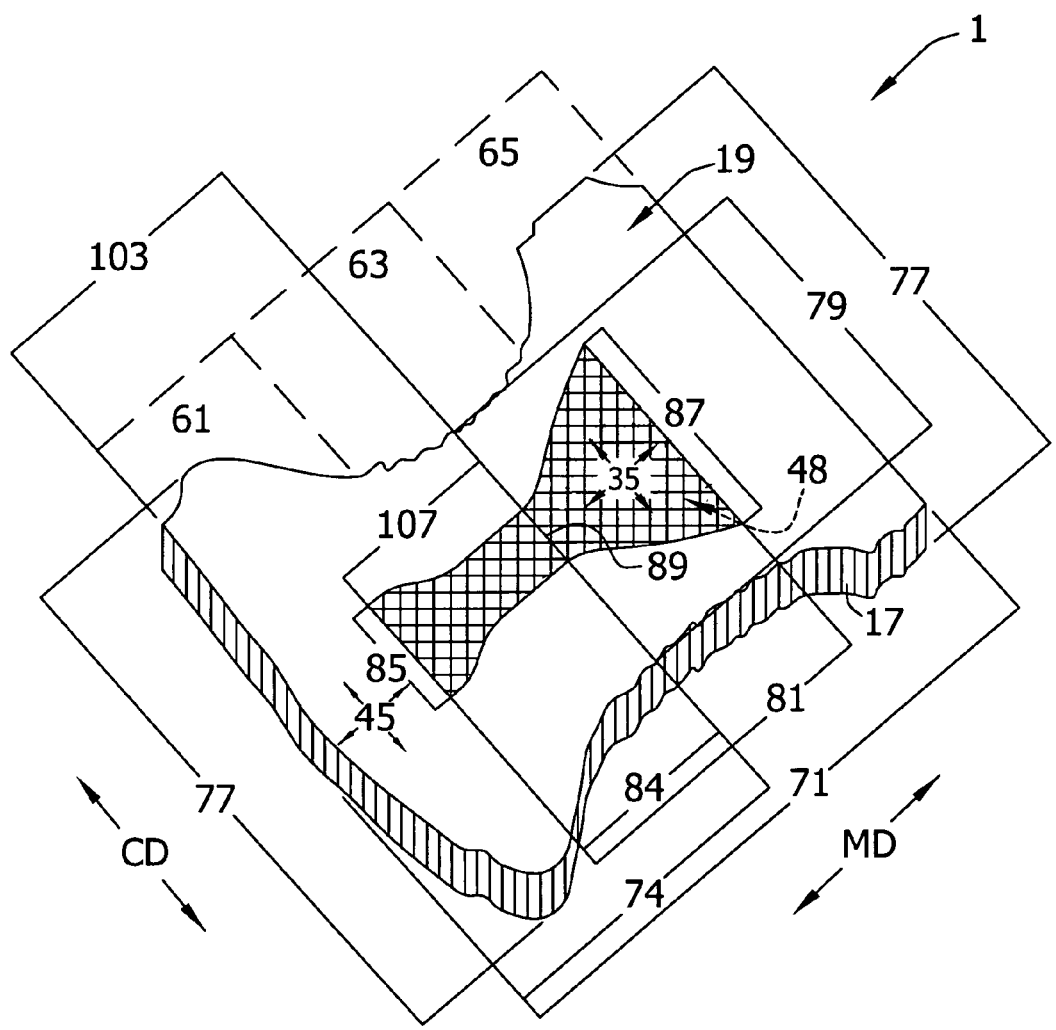
FIG. 4 illustrates a partial diaper assembly of the present invention.

FIG. 4 is an isometric top view of one embodiment of the diaper 1 in an extended, flat condition with all elastic contractions and gathers removed illustrating the absorbent core 3 affixed to the outer cover 17. The bodyside liner 5 is not shown. The diaper 1 of the present embodiment includes the back portion 65, the front portion 61 and the middle portion 63 interconnecting the back portion 65 and the front portion 61. The absorbent core 3 is affixed to the inner surface 19 of the outer cover 17 of the diaper 1. The absorbent core 3 has a first absorbent core length 81 and a second absorbent core length 84, which run along the machine direction of the chassis 2 and a first absorbent core width 85, a second absorbent core width 87 and an intermediate absorbent core width 89 which run along the cross-machine direction of the chassis 2. Both the second absorbent core length 84 of the absorbent core 3 and a function of the first absorbent core width 85, and the intermediate absorbent core width 89 of the absorbent core 3 essentially define the surface area 35 of the front one-half portion 107 of the absorbent core 3. The stretchable chassis 2 has a first chassis length 71 and a second chassis length 74 which run along the machine direction of the diaper 1 and a first chassis width 77 and a second chassis width 79 which run along the cross-machine direction of the diaper 1. Both the second chassis length 74 of the chassis 2 and a function of the first chassis width 77 and the second chassis width 79 of the stretchable chassis 2 essentially define the front one-half portion 103 of the surface area 45 of the stretchable chassis 2.

The non-stretch and/or low stretch nature of the absorbent core 3 creates drag on the stretchable surface area 45 of the chassis 2 at the points of fixation of the second surface 48 of the absorbent core 3 to the inner surface 19 of the outer cover 17, at the points of fixation of the first surface 47 of the absorbent core 3 to the inner surface 16 of the bodyside liner 5, or both, in the front one-half portion 103 of the stretchable chassis 2.

Extensibility in the front one-half portion 103 of the stretchable chassis 2 may be desirable for enhanced fit and comfort of the wearer especially if, for example, the receiving mechanism located on the front portion 61 edge of the outer cover 17 is also made of stretchable material. That is, if the entire second surface 48 of the front one-half portion 107 of the absorbent core 3 is affixed or laminated to the inner surface 19 of the outer cover 17, then the extensible capacity of the corresponding surface area 45 of the front one-half portion 103 of the stretchable chassis 2 may be significantly reduced by the entire surface area 35 of the front one-half portion 107 of the absorbent core 3.

A proportionally reduced surface area 35 of the front one-half portion 107 of the absorbent core 3 will proportionally increase the corresponding surface area 45 in the front one-half portion 103 of the stretchable chassis 2 that is unencumbered by the absorbent core 3, thus increasing the surface area 45 that is able to stretch around the wearer creating greater comfort, aesthetics and fit for the wearer. Although adequate absorbency in the front one-half portion 103 of the stretchable chassis 2 is desirable because the crotch area where the liquid insult occurs is typically located about the front one-half portion 103 of the chassis 2, the reduction in the surface area 35 of the absorbent core 3 in the front one-half portion 107 of the stretchable chassis 2 is not so low as to compromise the performance of the absorbent core 3.

Whether the entire surface area 35 of the front one-half portion 107 of the absorbent core 3 is affixed to the bodyside liner 5, the outer cover 17, or both of the stretchable chassis 2, or whether selective fixed points of the front one-half portion 107 of the surface area 35 of the absorbent core 3 are affixed to the bodyside liner 5, the outer cover 17, or both of the chassis 2, a reduction in the size of the absorbent core 3 in the front one-half portion 103 increases the corresponding surface area 45 in the front one-half portion 103 of the stretchable chassis 2 that is uninhibited by the attachment points of the absorbent core 3 allowing at least greater cross machine direction extension of the stretchable chassis 2 in that area. This may eliminate or greatly reduce the need for pleating the chassis 2 in the cross machine direction and/or eliminate the need of a stretchable absorbent core 3.

Figure 5:
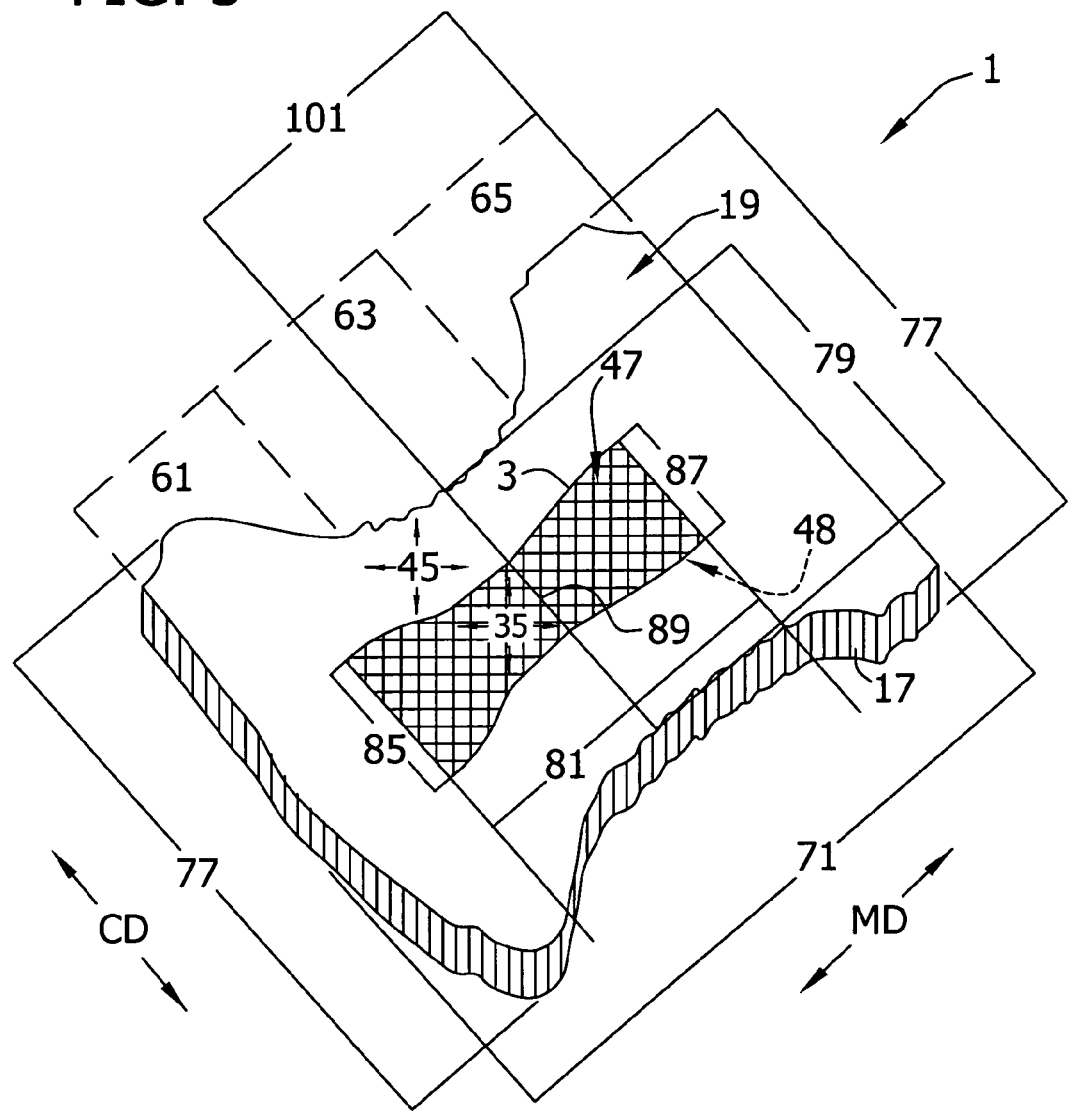
FIG. 5 illustrates a partial diaper assembly of the present invention.

FIG. 5 is an isometric top view of one embodiment of the diaper 1 in an extended, flat condition with all elastic contractions and gathers removed illustrating the absorbent core 3 affixed to the outer cover 17. The bodyside liner 5 is not shown. Absorbent core 3 is affixed to the inner surface 19 of the outer cover 17 of the diaper 1. The absorbent core 3 has a first absorbent core length 81, which runs along the machine direction of the chassis 2 and a first absorbent core width 85, a second absorbent core width 87 and an intermediate absorbent core width 89 which run along the cross-machine direction of the chassis 2. Both the first absorbent core length 81 and a function of the first absorbent core width 85, the second absorbent core width 87 and the intermediate absorbent core width 89 essentially define the surface area 35 of the absorbent core 3. The stretchable chassis 2 has a first chassis length 71, which runs along the machine direction of the diaper 1 and a first chassis width 77 and a second chassis width 79 which run along the cross-machine direction of the diaper 1. Both the first chassis length 71 of the chassis 2 and a function of the first chassis width 77 and the second chassis width 79 of the chassis 2 essentially define the surface area 45 of the chassis 2.

The non-stretch and/or low stretch nature of the absorbent core 3 creates drag on the stretchable surface area 45 of the stretchable chassis 2 at the points of fixation of the second surface 48 of the absorbent core 3 to the inner surface 19 of the outer cover 17, at the points of fixation of the first surface 47 of the absorbent core 3 to the inner surface 16 of the bodyside liner 5, or both. For example, if the entire second surface 48 of the absorbent core 3 is affixed or laminated to the inner surface 19 of the outer cover 17, then the extensible capacity of the surface area 45, which includes the back portion 65, the middle portion 63 and the front portion 61, are significantly reduced by the entire surface area 35 of the absorbent core 3.

In particular, extensibility is critical in the back one-half portion 101 of the stretchable chassis 2. This is because as the diaper 1 is applied to the wearer, the caregiver tends to pull on the fasteners 20, typically located on the outside edges of the outer cover 17 of the back portion 65, to better fit the diaper 1 around the waist of the wearer. The pulling on the fasteners 20 create stretch tensions on the surface area 45 of the back portion 65 of the stretchable chassis 2.

A proportionally reduced surface area 35 of the absorbent core 3 will proportionally increase the corresponding surface area 45 of the stretchable chassis 2 that is unencumbered by the absorbent core 3, thus increasing the corresponding surface area 45 that is able to stretch about the wearer. The reduction in the surface area 35 of the stretchable chassis 2 does not compromise the performance of the absorbent core 3. As stated above, the reduction in the surface area 35 of the back one-half portion 105 of the absorbent core 3 does not compromise the performance of the absorbent core 3 as the absorbent core 3 in the back one-half portion 101 of the chassis 2 does not play a vital role of absorbency, but rather, enhances the fit of the diaper 1 about the buttocks and waist of the wearer. Further, in the present embodiment, the surface area 35 of the absorbent core 3 in the front one-half portion 103 of the stretchable chassis 2 is not so reduced as to adversely affect the absorbency characteristics of the absorbent core 3 of the diaper 1.

Whether the entire surface area 35 of the absorbent core 3 is affixed to the bodyside liner 5, the outer cover 17, or both of the chassis 2, or whether selective fixed points of the surface area 35 of the absorbent core 3 are affixed to the bodyside liner 5, the outer cover 17, or both of the chassis 2, a reduction in the size of the absorbent core 3 increases the corresponding surface area 45 that is uninhibited by the attachment points of the absorbent core 3 allowing at least greater cross machine direction extension of the stretchable chassis 2. This may eliminate or greatly reduce the need for pleating chassis 2 in the cross machine direction and/or eliminate the need of a stretchable absorbent core 3.

The preferred embodiment of the present invention desirably includes a percentage ratio of the surface area 35 of the back one-half portion 105 of absorbent core 3 to the corresponding surface area 45 of the back one-half portion 101 of the stretchable multilayer chassis 2 that is preferably less than about 50%, alternately, less than about 40%, in another alternative, less than about 30%, in still another alternative, less than about 20%, and in still another alternative, less than about 15%.

An alternate embodiment of the present invention may include a percentage ratio of the surface area 35 of the front one-half portion 107 of absorbent core 3 to the corresponding surface area 45 of the front one-half portion 103 of the stretchable multilayer chassis 2 that is preferably less than about 50%, less than about 40%, less than about 30%, less than about 20%, or less than about 15%.

In another alternate embodiment of the present invention, the percentage ratio of the entire surface area 35 of the absorbent core 3 to the entire corresponding surface area 45 of the stretchable multilayer chassis 2 is preferably less than about 50%, less than about 40%, less than about 30%, less than about 20%, or less than about 15%.

The ratios of the surface area 35 of the absorbent core 3 to the corresponding surface area 45 of the chassis 2 as described above, advantageously improve the stretch characteristics of the bodyside liner 5 and the outer cover 17 to provide improved appearance, fit and leakage containment.

Methods of manufacturing the disposable absorbent article of the present invention, methods of manufacturing individual components useful to make the disposable absorbent article of the present invention, as well as methods of using the disposable absorbent article of the present invention are disclosed, e.g., in U.S. Pat. Nos. 6,321,557; 6,193,701; 6,129,720; 6,060,115; 5,595,618; 5,883,028; 5,540,796; 5,509,915; 5,496,298; 5,490,846; 5,486,166; 5,192,606; 5,176,668; 5,116,662; 5,114,781; 4,965,122; 4,798,603; 4,777,073; 4,704,116; U.S. patent application Ser. Nos. 09/698,512; 09/460,490; 09/455,513 and references cited therein.

Material Elongation and Deformation Tensile Test

A suitable technique for determining the amount of elongation, retractive force and or permanent deformation of a selected component or material can employ ASTM Standard Test Method D882 (Tensile Method for Tensile Properties of Thin Plastic Sheeting) dated December 1995, with the following particulars.

Equipment
1. Tensile tester capable of obtaining a peak load and equipped with an appropriate load cell. A suitable tensile testing system is a Sintech Tensile Tester, commercially available from MTS Sintech, Research Triangle Park, N.C., under the trade designation Model 1/G equipped with Sintech Testworks™ Version 3.10 Software.
2. Pneumatic-action grips having a 0.5 by 4 inch grip face.
3. Test facility having a temperature of 23+1° C., and a relative humidity of 50+2 percent.

The test sample width is perpendicular to the direction of the tensile force applied during the testing. With regard to the shown configurations, for example, the test sample "width" generally corresponds to the length-wise dimension of outer cover 17 along the longitudinal direction of the diaper 1. The initial separation of the jaws of the tensile tester is 3 inches (76.2 mm) at a tensile force of about 1 gram force per inch of width of the test sample, and the moving jaw is moved at a constant rate of 127 mm/min. The moving jaw is stopped at an extension where the tensile force equals 100 grams force per inch of width of the test sample, held at that extension for a period of 2 minutes, and then returned back to its initial tensile force of about 1 gram force per inch of width of the test sample at a rate of 127 mm/min. The percentage of elongation, extension or permanent deformation can be determined in accordance with the following formula:

$$100*(L-LO)/(LO);$$

where:
L=either a) extended length for elongation or extension or b) post extended length for set or deformation, and
LO=initial length.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled. All patents, patent documents, and references cited and disclosed herein are incorporated by reference herein.

EXAMPLES

The present invention utilizes a decreased ratio of the surface area of the absorbent core 3 with respect to the corresponding surface area of the chassis 2 to enhance user comfort, aesthetics and fit without sacrificing absorbent performance. A decrease in the surface area 35 of the absorbent core 3 proportionally increases the stretchability of the surface area 45 of the chassis 2 that is unencumbered by an affixed absorbent core 3. The determination of appropriate ratios of the absorbent core 3 with respect to the stretchable chassis 2 includes calculating the various surface areas 35 of the absorbent core 3 as a percent ratio of the surface area 45 of the stretchable chassis 2. It should be noted that the ratio of the surface area 35 of the absorbent core 3 relates to the absorbent core 3 itself and not to any tissue material, wrapsheets or the like that may surround and/or encompass the absorbent core 3. This is to eliminate the possibility of calculating an inaccurate surface area 35 of the absorbent core 3 as tissue material, wrapsheets or the like tend to vary in width.

Figure 6:
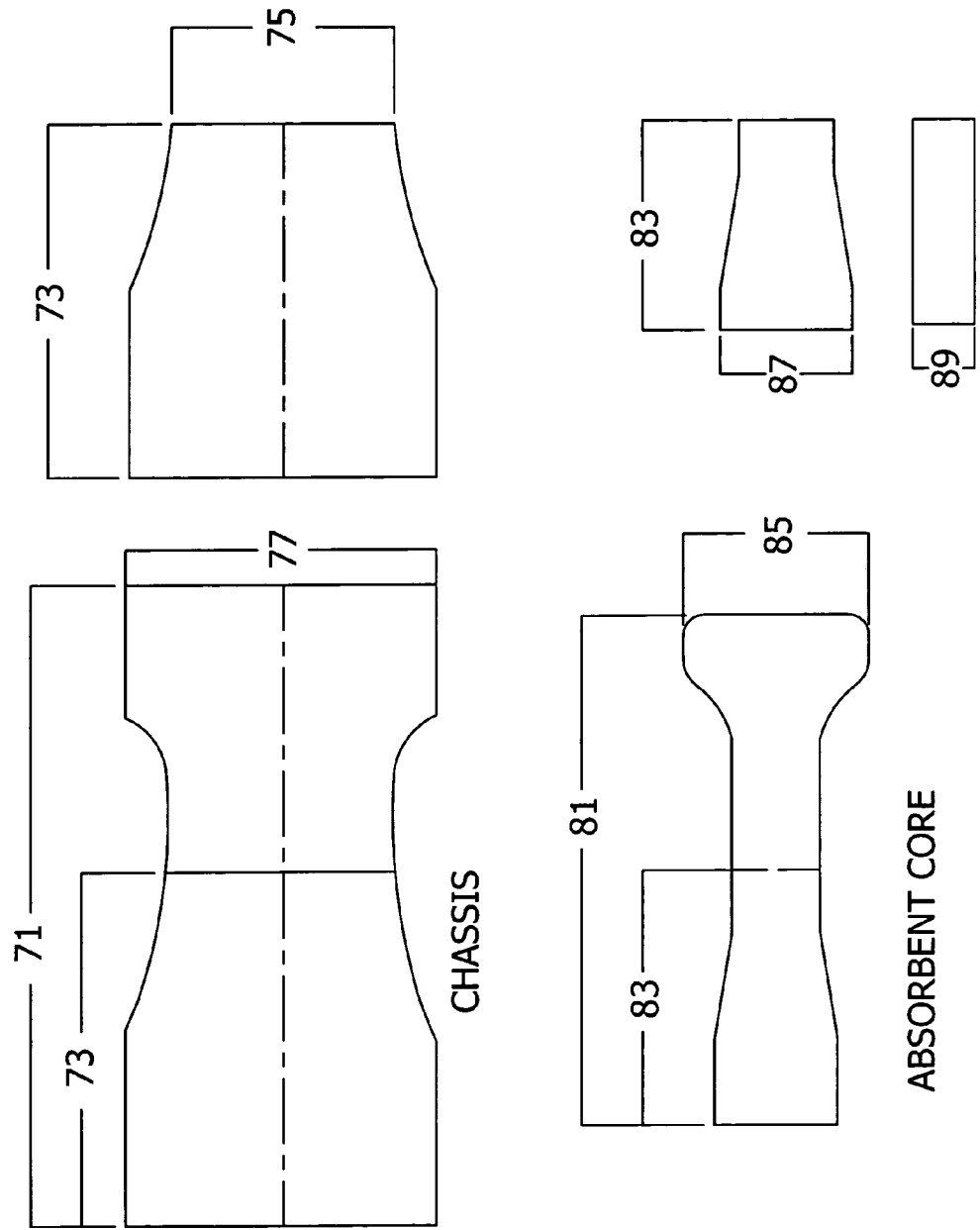
FIG. 6 illustrates specific embodiments of the present invention.

FIG. 6 provides an illustration of the various lengths and widths utilized in the present invention to calculate the surface area 35 of the absorbent core 3. Specifically, the surface area 35 of the back one-half portion 105 of the absorbent core 3, the front one-half portion 107 of the absorbent core 3 and the entire surface area 35 of the absorbent core 3. Further, FIG. 6 provides a non-value exemplary illustration of the various lengths and widths utilized in the present invention to calculate the surface area 45 of the stretchable chassis 2. Specifically, the surface area 45 of the back one-half portion 101 of the stretchable chassis 2, the front one-half portion 103 of the stretchable chassis 2 and the entire surface area 45 of the stretchable chassis 2.

For example, the back one-half portion of the surface area of the chassis 2 is determined by multiplying the second chassis length 73 times the function of the first chassis width 77 and the second chassis width 79; and the back one-half portion of the surface area of the absorbent core 3 is determined by multiplying the second absorbent core length 83 times the function of the second absorbent core width 87 and the intermediate absorbent core width 89.

In addition, the front one-half portion of the surface area of the chassis 2 is determined by multiplying the difference between the first chassis length 71 and the second chassis length 73 times the function of the second chassis width 79 and the first chassis width 77 of the chassis 2; and the front one-half portion of the surface area of the absorbent core 3 is determined by multiplying the difference between the first absorbent core length 81 and the second absorbent core length 83 times the function of the first absorbent core width 85 and the intermediate absorbent core width 89 of the absorbent core 3.

Further, the entire surface area of the chassis 2 is determined by multiplying the first chassis length 71 times the function of the second chassis width 79 and the first chassis width 77; and the entire surface area of the absorbent core 3 is determined by multiplying the first absorbent core length 81 times a function of the first absorbent core width 85, the second absorbent core width 87 and the intermediate absorbent core width 89.

Figure 8:
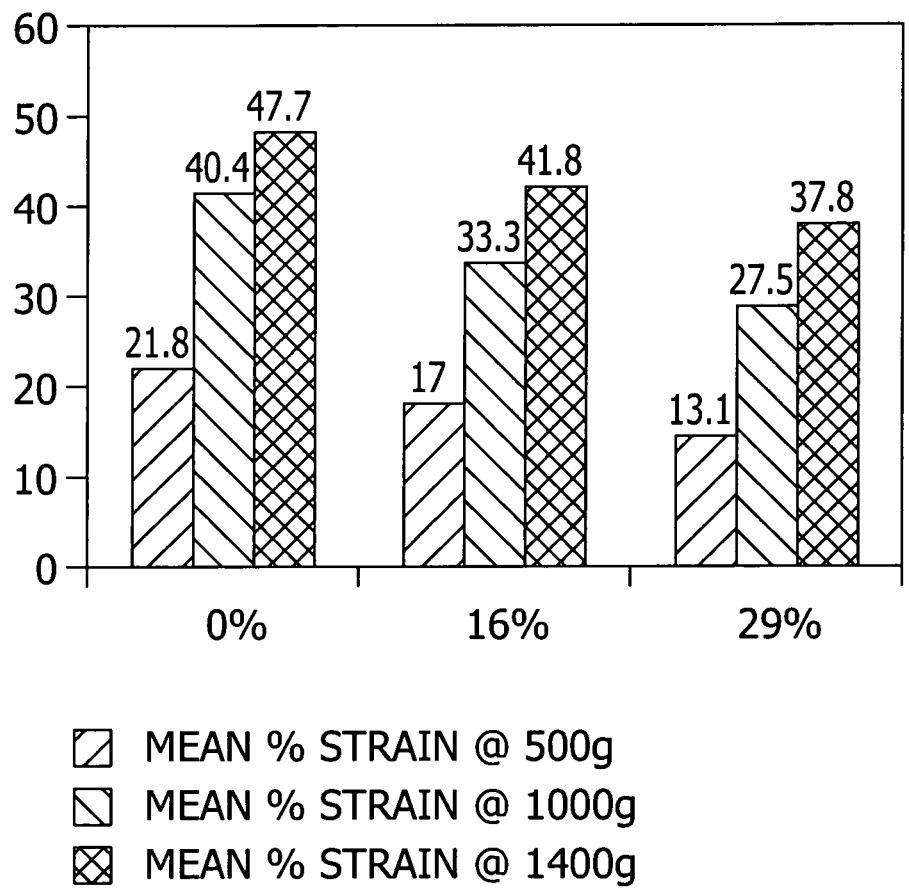
FIG. 8 illustrates specific characteristics for specific embodiments of the present invention.

FIGS. 7-8 provide a test comparison of the percent ratio of the surface area 35 of the non-stretch and/or low stretch absorbent core 3 relative to the corresponding surface area 45 of the stretchable chassis 2 at 29%, 16% and 0%. The tension of each percent ratio was derived from a combination of each percent area 35 of the non-stretch and/or low stretch absorbent core 3 relative to the corresponding surface area 45 of the extensible chassis 2 ratio. The ratio of the area of the non-stretch and/or low stretch absorbent core 3 relative to the area of the extensible chassis 2 was determined by calculating the amount of the absorbent core 3 to the amount of the extensible chassis 2 (i.e., at least the outer cover 17 and the bodyside liner 5). The percent strain at 500 grams, 1000 grams and 1400 grams were made on a Sintech Tensile Tester.

Test Method

Absorbent articles were prepared in accordance with the present invention. Necked laminates suitable for the stretchable chassis 2 of the present invention were adhered to each other. Specifically, the chassis 2 of the diaper 1 includes a stretchable outer cover 17 adhered to a bodyside liner 5. The absorbent core 3 is sandwiched between the outer cover 17 and the bodyside liner 5 and affixed to the chassis 2 thereto. The outer cover 17 includes a 35-45% necked PP Spunbond nonwoven material and a XP-8600 PLIANT film adhered to each other using National Starch adhesive at an add on rate of 4 gsm. The bodyside liner 5 includes a 45% necked 0.4 osy polypropylene spunbond nonwoven material. The absorbent core 3 includes Alliance CR1654 bleached softwood pulp fiber (16% hardwood), DOW XUS 40675.00 Superabsorbent Polymer, and Barrier Sheet Tissue. The stretchable outer cover 17, the bodyside liner 5 and the absorbent core 3 are adhered to each other with an adhesive ATO Findley-H2525A.

Grab Tensile Test:

The grab tensile test is a measure of breaking strength and elongation or strain of a fabric when subjected to unidirectional stress. This test is known in the art and conforms to the specifications of Method 5100 of the Federal Test Methods Standard 191A. The results are expressed in pounds or grams to break and percent stretch before breakage. Higher numbers indicate a stronger, more stretchable fabric. The term "load" means the maximum load or force, expressed in units of weight, required to break or rupture the specimen in a tensile test. The term "total energy" means the total energy under a load versus elongation curve as expressed in weight-length units. The term "elongation" means the increase in length of a specimen during a tensile test. The grab tensile test uses two clamps, each having two jaws with each jaw having a facing in contact with the sample. The clamps hold the material in the same plane, usually vertically, separated by 3 inches (76 mm) and move apart at a specified rate of extension. Values for grab tensile strength and grab elongation are obtained using a sample size of the chassis 2, for example, the second chassis length 73 X the function of the first chassis width 77 and the second chassis width 79 (i.e., the back one-half portion of the surface area of the chassis 2), and a sample size of the absorbent core 3, for example, second absorbent core length 83 X the function of the second absorbent core width 87 and the intermediate absorbent core width 89 (the back one-half portion of the surface area of the absorbent core 3) with a jaw facing size of 1 inch (25 mm) by 1 inch, and a constant rate of extension of 300 mm/min. The sample is wider than the clamp jaws to give results representative of effective strength of fibers in the clamped width combined with additional strength contributed by adjacent fibers in the fabric. The specimen is clamped in, for example, a Sintech 2 tester, available from the Sintech Corporation, 1001 Sheldon Dr., Cary, N.C. 27513, an Instron Model™, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154. This closely simulates fabric stress conditions in actual use. Results are reported as an average of three specimens and may be performed with the specimen in the cross direction (CD), the machine direction (MD), or both.

Specifically, where the ratio of the surface area 35 of the back one-half portion 105 of the absorbent core 3 to the corresponding surface area 45 of the back one-half portion 101 of the stretchable chassis 2 is 29%, the chassis has a mean strain of 13.1% at 500 g, a mean strain of 27.5% at 1000 g, and a mean strain of 37.8% at 1400 g. Where the ratio of the surface area 35 of the back one-half portion 105 of the absorbent core 3 to the corresponding surface area 45 of the stretchable back one-half portion 101 of the chassis 2 is 16%, the chassis has a mean strain of 17.0% at 500 g, a mean strain of 33.3% at 1000 g, and a mean strain of 41.8% at 1400 g. Where the ratio of the surface area 35 of the back one-half portion 105 of the absorbent core 3 to the surface area 45 of the stretchable back one-half portion 101 of the chassis 2 is 0%, the chassis has a mean strain of 21.8% at 500 g, a mean strain of 40.4% at 1000 g, and a mean strain of 47.7% at 1400 g.

The above test results are derived from a diaper 1 wherein the absorbent core 3 is affixed to the chassis 2. The above test results indicate that as the percent ratio of the surface area 35 of the back one-half portion 105 of the absorbent core 3 to the corresponding surface area 45 of the back one-half portion 101 of the stretchable chassis 2 decreases, the stretchability of the chassis 2 increases. For example, the mean percentage strains at 500 g, at 1000 g, and at 1400 g significantly increase when the ratio of the surface area 35 of the back one-half portion 105 of the absorbent core 3 to the corresponding surface area 45 of the stretchable back one-half portion 101 of the chassis 2 is at 16% than when at 29%. Accordingly, a reduction in the size of the absorbent core 3 increases the corresponding surface area 45 in the back one-half portion 101 of the stretchable chassis 2 that is uninhibited by the attachment points of the absorbent core 3 allowing enhanced stretchability of the stretchable chassis 2 therein reducing the cost and complexity of manufacturing the diaper 1 of the present invention and improving the appearance, fit and leakage containment for the wearer.

What is claimed is:

1. A disposable absorbent article having a longitudinal axis, a lateral axis, and a lateral centerline generally defining longitudinal front and back regions of the article, said article having a front end, a back end, a front portion, a back portion, and a middle portion interconnecting the front and back portions, said article comprising:
a liner adapted for contiguous relationship with a wearer's body;
an outer cover in generally opposed relationship with the liner, the outer cover having a length and a width and being stretchable along substantially the entire length of the outer cover; the article having a surface area defined at least in part by said outer cover; and
an absorbent core disposed between the liner and the outer cover and having a width, a length, a thickness, a front edge, a back edge, and a surface area defined by the width and the length, the surface area being less than 50% of the surface area of the article, the absorbent core being disposed at least in said front portion and said middle portion of the article, the surface area of the absorbent core being greater in said front portion of the article than in said back portion and said middle portion, the surface area of the absorbent core being greater in said middle portion of the article than in said back portion, the front edge of the absorbent core being in a closer proximity to the front end of the article than the back edge of the absorbent core is to the back end of the article, at least a portion of the absorbent core being bonded to said outer cover, wherein reducing the surface area of the absorbent core increases the surface area of the article that is uninhibited by an attachment point of the absorbent core.

2. A disposable absorbent article as set forth in claim 1 wherein the liner has a length and a width, said liner being stretchable along substantially the entire length of the liner.

3. A disposable absorbent article as set forth in claim 2 wherein said outer cover has a length and a width, said outer cover being stretchable along substantially the entire length of the outer cover.

4. The disposable absorbent article as set forth in claim 1, wherein the outer cover is stretchable along the entire width of the outer cover.

5. The disposable absorbent article as set forth in claim 4 wherein said outer cover is capable of lateral elongation of about 10 percent when the article is subjected to a laterally directed tensile force of about 100 gmf per inch (per 2.54 cm) of width of said outer cover.

6. The disposable absorbent article as set forth in claim 4 wherein said outer cover is capable of lateral elongation of about 20 percent when the article is subjected to a laterally directed tensile force of about 100 gmf per inch (per 2.54 cm) of width of said outer cover.

7. The disposable absorbent article as set forth in claim 4 wherein said outer cover is capable of lateral elongation of about 30 percent when the article is subjected to a laterally directed tensile force of about 100 gmf per inch (per 2.54 cm) of width of said outer cover.

8. The disposable absorbent article as set forth in claim 4 wherein said outer cover is capable of lateral elongation of about 40 percent when the article is subjected to a laterally directed tensile force of about 100 gmf per inch (per 2.54 cm) of width of said outer cover.

9. The disposable absorbent article as set forth in claim 4 wherein said outer cover is capable of substantially permanent elongation laterally of said article whereby the width of said outer cover is increased at least about 17 percent when the article is subjected to a laterally directed tensile force of about 100 gmf per inch (per 2.54 cm) of width of said outer cover.

10. The disposable absorbent article as set forth in claim 4 wherein said outer cover is capable of substantially permanent elongation laterally of said article whereby the width of said outer cover is increased at least about 30 percent when the article is subjected to a laterally directed tensile force of about 100 gmf per inch (per 2.54 cm) of width of said article.

11. The disposable absorbent article as set forth in claim 4 wherein the outer cover comprises a necked laminate having at least one layer of a non-elastic neckable material and at least one layer of a non-elastic film.

12. The disposable absorbent article as set forth in claim 4, wherein the outer cover is elastic.

13. The disposable absorbent article as set forth in claim 12, wherein the outer cover is elastic at least laterally of the article.

14. The disposable absorbent article as set forth in claim 12 wherein the outer cover comprises a polypropylene spunbond laminated with styrene isoprene styrene based adhesive.

15. The disposable absorbent article as set forth in claim 1 wherein said front half of the article has a surface area and at least a portion of the absorbent core extends into the front half of the article, said portion of the absorbent core having a surface area which is less than about 50% of the surface area of the front half of said article.

16. The disposable absorbent article as set forth in claim 15 wherein said article is a diaper.

17. The disposable absorbent article as set forth in claim 15, wherein the surface area defined by said portion of the absorbent core is less than or equal to about 40% of the surface area of the front half of said article.

18. The disposable absorbent article as set forth in claim 15 wherein the surface area defined by said portion of the absorbent core is less than or equal to about 30% of the surface area of the front half of said article.

19. A disposable absorbent article having a longitudinal axis, a lateral axis, and a lateral centerline generally defining longitudinal front and back regions of the article, said article having a front end, a back end, a front portion, a back portion, and a middle portion interconnecting the front and back portions, the article comprising:
a liner adapted for contiguous relationship with a wearer's body, the liner having a length and a width and being stretchable along substantially the entire length of the liner;
an outer cover in generally opposed relationship with the liner;

the article having a surface area defined at least in part by said liner; and an absorbent core disposed between the liner and the outer cover and having a width, a length, a thickness, a front edge, a back edge, and a surface area defined by the width and the length, the surface area being less than 50% of the surface area of the article, the absorbent core being disposed at least in said front portion and said middle portion of the article, the surface area of the absorbent core being greater in said front portion of the article than in said back portion and said middle portion, the surface area of the absorbent core being greater in said middle portion of the article than in said back portion, the front edge of the absorbent core being in a closer proximity to the front end of the article than the back edge of the absorbent core is to the back end of the article, at least a portion of the absorbent core being bonded to said liner, wherein reducing the surface area of the absorbent core increases the surface area of the article that is uninhibited by an attachment point of the absorbent core.

20. A disposable absorbent article having a longitudinal axis, a lateral axis, and a lateral centerline generally defining longitudinal front and back regions of the article, said article having a front end, a back end, a front portion, a back portion, and a middle portion interconnecting the front and back portions, the article comprising:

a liner adapted for contiguous relationship with a wearer's body;

an outer cover in generally opposed relationship with the liner, at least one of said liner and said outer cover being stretchable in at least one direction, the article having a surface area defined at least in part by at least one of said liner and said outer cover; and an absorbent core disposed between the liner and the outer cover and having a width, a length, a thickness, a front edge, a back edge, and a surface area defined by the width and the length, the surface area being less than 50% of the surface area of the article, the absorbent core being disposed at least in said front portion and said middle portion of the article, the surface area of the absorbent core being greater in said front portion of the article than in said back portion and said middle portion, the surface area of the absorbent core being greater in said middle portion of the article than in said back portion, the front edge of the absorbent core being in a closer proximity to the front end of the article than the back edge of the absorbent core is to the back end of the article, said at least one of said liner and said outer cover extending beyond the front and back edges of the absorbent core and being stretchable adjacent said front and back edges, wherein reducing the surface area of the absorbent core increases the surface area of the article that is uninhibited by an attachment point of the absorbent core.

* * * * *